United States Patent
Rill et al.

(10) Patent No.: US 12,070,424 B2
(45) Date of Patent: Aug. 27, 2024

(54) SYSTEMS AND METHODS FOR SHORT PULSE LASER EYE SURGERY

(71) Applicant: Carl Zeiss Meditec AG, Jena (DE)

(72) Inventors: Michael Stefan Rill, Jena (DE); Delbert Peter Andrews, Oberkochen (DE); Tobias Damm, Munich (DE); Robert Pomraenke, Jena (DE); Jens Ringling, Berlin (DE); Thomas Wollweber, Eckartsberga (DE); Stephan Oestreich, Berlin (DE); Michael Bergt, Weimar (DE); Rupert Menapace, Vienna (AT); Ekkehard Fabian, Rosenheim (DE); Evangelos Papastathopoulos, Jena Ludwigsburg (DE); Martin Kühner, Bad Klosterlausnitz (DE); Dietmar Steinmetz, Bucha (DE); Holger Heinz, Jena (DE); Sascha Koch, Jena Isserstedt (DE); Stephan Laqua, Jena (DE); Thomas Nobis, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 770 days.

(21) Appl. No.: 16/903,758

(22) Filed: Jun. 17, 2020

(65) Prior Publication Data
US 2020/0330278 A1 Oct. 22, 2020

Related U.S. Application Data

(63) Continuation of application No. 15/518,696, filed as application No. PCT/EP2015/073390 on Oct. 9, 2015, now Pat. No. 10,722,399.

(30) Foreign Application Priority Data

Oct. 17, 2014 (DE) .................... 10 2014 221 174.3
Oct. 8, 2015 (DE) .................... 10 2015 219 507.4

(51) Int. Cl.
*A61F 9/009* (2006.01)
*A61B 3/10* (2006.01)
(Continued)

(52) U.S. Cl.
CPC .......... *A61F 9/00834* (2013.01); *A61B 3/102* (2013.01); *A61B 3/13* (2013.01);
(Continued)

(58) Field of Classification Search
CPC .. A61F 9/008; A61F 9/00802; A61F 9/00825; A61F 9/00834;
(Continued)

(56) References Cited

U.S. PATENT DOCUMENTS

| 5,246,435 A | 9/1993 | Bille et al. |
| 5,336,215 A * | 8/1994 | Hsueh ..................... A61F 9/009 606/4 |

(Continued)

FOREIGN PATENT DOCUMENTS

| DE | 10 2010 022 298 A1 | 12/2011 |
| DE | 10 2011 085 046 A1 | 4/2013 |

(Continued)

OTHER PUBLICATIONS

Application and File History for U.S. Appl. No. 15/518,696, filed Apr. 12, 2017. Inventors: Michael Stefan Rill et al.

(Continued)

*Primary Examiner* — Ahmed M Farah
(74) *Attorney, Agent, or Firm* — DeWitt LLP

(57) ABSTRACT

A system for short pulse laser eye surgery and a short pulse laser system, in which a beam guidance device passes through a corresponding articulated arm, and through an applicator head and a microscope head of the system, which is movable in a three-dimensional volume both independently of one another as well as connected to each other. The (Continued)

system also includes an easy to use patient interface with a one-piece contact element, a computer program product for methods of the incision guidance and sequentially operating referencing methods with patient interfaces containing markings.

19 Claims, 20 Drawing Sheets

(51) Int. Cl.
    *A61B 3/13*     (2006.01)
    *A61B 90/25*     (2016.01)
    *A61F 9/008*     (2006.01)

(52) U.S. Cl.
    CPC .......... *A61B 90/25* (2016.02); *A61F 9/00825* (2013.01); *A61F 2009/00855* (2013.01); *A61F 2009/00861* (2013.01); *A61F 2009/0087* (2013.01); *A61F 2009/00872* (2013.01); *A61F 2009/00882* (2013.01); *A61F 2009/00897* (2013.01)

(58) Field of Classification Search
    CPC .. A61F 2009/00855; A61F 2009/00861; A61F 2009/0087; A61F 2009/00872; A61F 2009/00885; A61F 2009/00897; A61F 9/009; A61F 9/00804; A61F 2009/00878; A61F 2009/00882; A61B 18/20; A61B 2018/2015; A61B 2018/2035; A61B 2018/20351; A61B 90/20; A61B 90/25; A61B 90/30; A61B 90/35; A61B 3/102; A61B 3/103; A61B 3/107; A61B 3/13; A61B 18/18; A61B 18/203; A61B 18/2035; A61B 18/20351
    USPC ............................................ 606/4–6, 13, 166
    See application file for complete search history.

(56) References Cited

U.S. PATENT DOCUMENTS

| | | | |
|---|---|---|---|
| 6,019,472 A | 2/2000 | Koester et al. | |
| 6,325,792 B1 | 12/2001 | Swinger et al. | |
| 6,454,761 B1 | 9/2002 | Freedman | |
| 7,955,324 B2 * | 6/2011 | Melcher | A61F 9/009 606/5 |
| 8,500,723 B2 * | 8/2013 | Frey | A61F 9/009 606/4 |
| 9,849,031 B2 * | 12/2017 | Bischoff | A61F 9/0084 |
| 10,722,399 B2 * | 7/2020 | Rill | A61B 3/102 |
| 2002/0198516 A1 | 12/2002 | Knopp | |
| 2006/0195076 A1 | 8/2006 | Palankar et al. | |
| 2007/0173794 A1 | 7/2007 | Frey et al. | |
| 2009/0131921 A1 | 5/2009 | Kurtz et al. | |
| 2010/0094264 A1 * | 4/2010 | Rathjen | A61F 9/008 606/4 |
| 2012/0078241 A1 | 3/2012 | Gooding et al. | |
| 2012/0316544 A1 | 12/2012 | Horvath et al. | |
| 2013/0053837 A1 | 2/2013 | Kandulla et al. | |
| 2013/0102922 A1 | 4/2013 | Gooding | |
| 2013/0265545 A1 | 10/2013 | Buckland et al. | |
| 2014/0058367 A1 * | 2/2014 | Dantus | H01S 3/005 606/4 |
| 2014/0107634 A1 * | 4/2014 | Vogler | A61F 9/00825 606/6 |
| 2014/0364744 A1 * | 12/2014 | Wellhoefer | A61B 3/0083 600/407 |
| 2015/0077705 A1 | 3/2015 | Artsyukhovich | |
| 2015/0088103 A1 * | 3/2015 | Rathjen | A61F 9/009 606/4 |
| 2015/0190278 A1 * | 7/2015 | Gooding | A61F 9/008 606/4 |
| 2016/0089269 A1 | 3/2016 | Horvath | |
| 2017/0296384 A1 * | 10/2017 | Fleischmann | A61B 90/50 |
| 2018/0085257 A1 | 3/2018 | Horvath | |
| 2019/0269554 A1 * | 9/2019 | Goldshleger | A61F 9/009 |

FOREIGN PATENT DOCUMENTS

| | | |
|---|---|---|
| WO | WO 2008/098388 A1 | 8/2008 |
| WO | WO 2012/041347 A1 | 4/2012 |
| WO | WO 2012/170966 A1 | 12/2012 |
| WO | WO 20112/170966 A1 | 12/2012 |

OTHER PUBLICATIONS

PCT International Search Report for International Application No. PCT/EP2015/073390, mailed May 31, 2016, 6 pages.

Written Opinion for International Application No. PCT/EP2015/073390, mailed May 31, 2016, 9 pages.

English translation of PCT International Search Report for International Application No. PCT/EP2015/073390, mailed May 31, 2016, 2 pages.

DE Search Report for DE 10 2014 221 174.3, dated Jun. 29, 2015, 9 pages.

English translation of PCT International Preliminary Report on Patentability and Written Opinion for International Application No. PCT/EP2015/073390, mailed Apr. 27, 2017, 10 pages.

* cited by examiner (a) x/y-positioning of the objective, so that the to x/y-focal positions to be projected are within the field of view (b) x/y-scanning of the focal positions of the short pulse laser radiation by x/y-mirror scanner, if necessary by sequentially varying z-positioning of the focal position along with or parallel the optical axis (a) simultaneous movement of the objective in a lateral direction x or y and movement of the divergence varying lens system for adjusting the z-focal position if necessary (b) superposition of the focus position in another lateral direction y or x by a fast mirror scanner of the x/y-scanning system

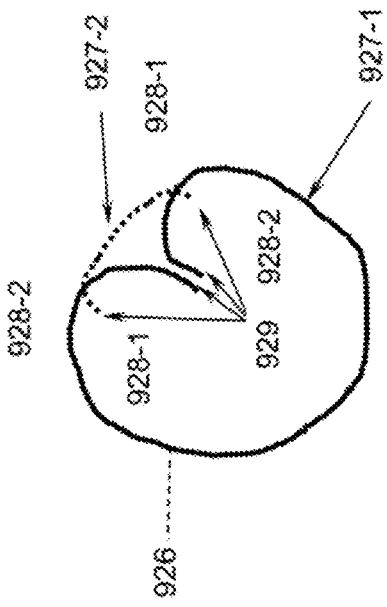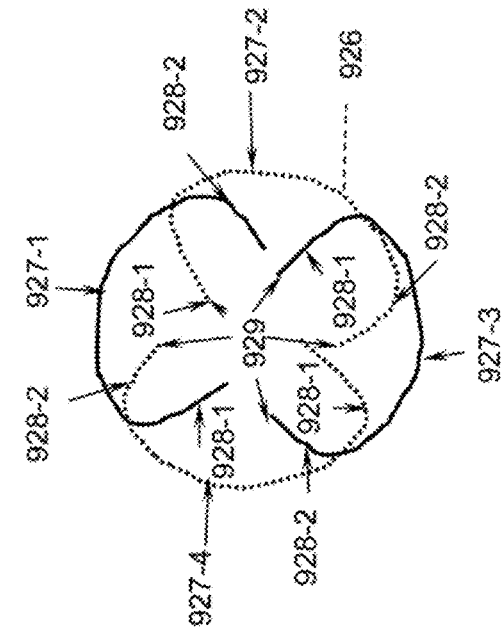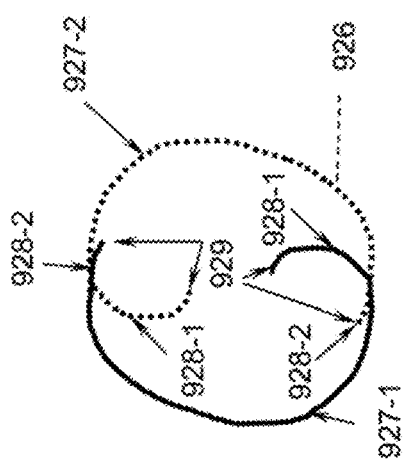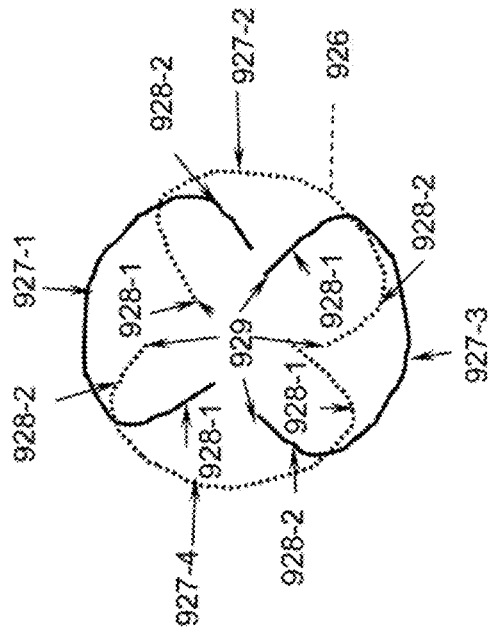
Fig. 17a
Fig. 17c
Fig. 16
Fig. 17b (1) Recording a first image of the anterior chamber of the eyeball under green illumination in undocked state of the applicator head, but with a distance of the applicator head from the eye of equal or less 3cm

↓

(2) Registering the position of a marking of the contact element of a patient interface relative to structures of the sclera of the first image

↓

(3) Recording a second image of the anterior chamber of the eyeball in docked state of the applicator head

↓

(4) Aligning the short pulse laser incisions by means of the second image using the position of the marking of the contact element and the registration obtained in step (2)

↓

(optional 5) Registering the position of the marking of the contact element with respect to remaining visible reference markings in the second image

↓

(optional 6) Aligning the short pulse laser incisions by means of the positions of the marker of the second image and/or the remaining structures in the second image, provided that the registration of the position of the marking compared to the visible reference markings of the eye in the second image does not deviate from a predetermined amount of the registration of the position of the marking with respect to the reference markings of the eye in the first image

Fig. 20

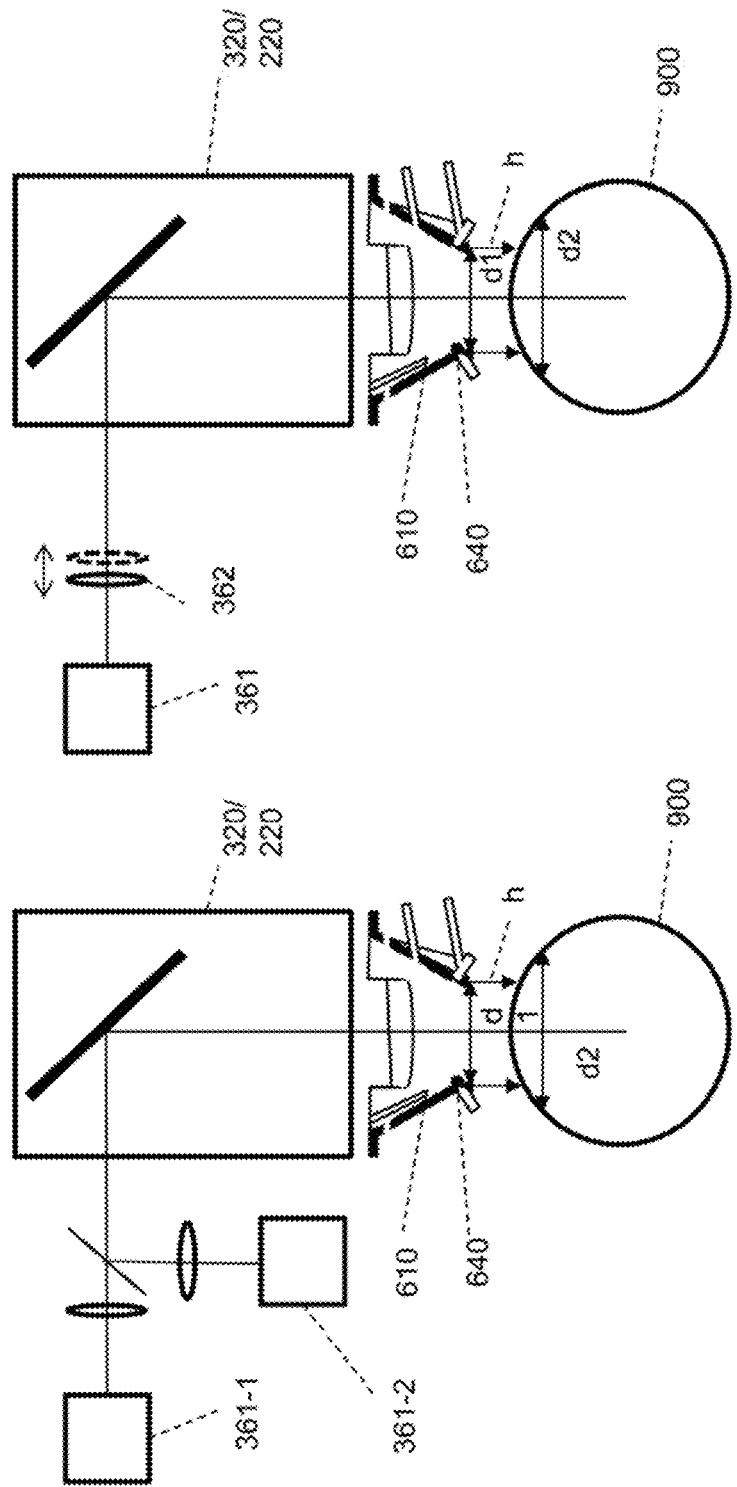

SYSTEMS AND METHODS FOR SHORT PULSE LASER EYE SURGERY

RELATED APPLICATION

This application is a continuation of application Ser. No. 15/518,696, filed Apr. 12, 2017, entitled "Systems and Methods for Short Pulse Laser Eye Surgery," which in turn is a National Phase entry of PCT Application No. PCT/EP2015/073390 filed Oct. 9, 2015, which claims the benefit of priority to German Application No. 10 2014 221 174.3, filed Oct. 17, 2014, and German Application No. 10 2015 219 507.4, filed Oct. 8, 2015, each of which is hereby fully incorporated herein by reference.

TECHNICAL FIELD

The present invention relates to a system for short pulse laser eye surgery with a short pulse laser source, beam guidance device and an applicator head for directing a short pulse laser radiation from the short pulse laser source to the eye to be operated on, a surgical microscope with a microscope head and a control unit, a housing and a first articulated arm on which the microscope head is arranged and a second articulated arm on which an applicator head is arranged, and with an interface at the applicator head and at the microscope head for mechanically and optically connecting or releasing the applicator head and the microscope head.

The invention also relates to a short pulse laser system for eye surgery with a short pulse laser source, a lens system varying the divergence of a short pulse laser radiation of the short pulse laser source, an x/y scanning system, an articulated arm and an objective movable in the x- and y-direction; a patient interface for fixing the relative position of an eye to an optical system for short pulse laser eye surgery and a computer program product for encoding a control unit of a short pulse laser system for eye surgery.

The invention further relates to a method for positioning an applicator head and a microscope head in a system for short pulse laser eye surgery, methods for the cut guidance with a short pulse laser system for eye surgery and referencing methods for various cuts and for an intraocular lens.

BACKGROUND

Cataract surgeries are the most commonly performed surgeries on the human eye and are therefore in the focus of continuous improvements or of the quality of the surgery result, efficiency in the surgery execution and minimization of risk. Through recent developments and progresses in ophthalmic femtosecond (fs) laser technology, especially in the area of refractive eye surgery, and of optical coherence tomography (OCT) as imaging technology, cataract surgeries are increasingly automated. Hereby, short pulse lasers are used to "cut" the eye tissue by application of photodisruption. This technology is hereinafter referred to as laser-assisted cataract surgery (LCS). According to current application principles, capsulotomy (circular incision of the anterior capsular bag of the eye lens), lens fragmentation (dividing the eye lens nucleus), access cuts in the cornea (main access and auxiliary cuts), and arcuate incisions (circular cuts for reducing a corneal astigmatism) are carried out within the scope of LCS, wherein the latter significantly goes beyond the extent of the classic cataract surgery, and touches the area of refractive eye surgery.

In U.S. Pat. No. 6,325,792 B1 it is suggested to focus pulses of a femtosecond laser into the eye lens in order to "liquefy" the eye lens—this corresponds to the abovementioned lens fragmentation—or to cut the capsulotomy. The positioning of the pulse focuses of the femtosecond laser thereby takes place by the use of ultrasonic imaging.

In U.S. Pat. No. 5,246,435 it is disclosed to focus pulses of a short pulse laser in a three-dimensional incision pattern into the natural lens of the eye, to separate the lens into fragments by application of the cuts and to liquefy it thereby.

In U.S. Pat. No. 6,454,761B1 it is suggested to use the optical coherence tomography (OCT) instead of ultrasound imaging for the automatic positioning of laser pulses in eye surgery operations on the cornea or other transparent structures, e.g. when removing a cataract in the eye lens.

Only a few years ago, the increasing maturity of the femtosecond laser technology and of the OCT technology permitted a combination and integration of these two technologies and the establishment of largely automated femtosecond laser systems in cataract surgery. For deflecting the femtosecond pulses, fixed objectives and fast mirror scanners for the lateral x/y-deflection of the laser beam in the eye are used on the one hand and slowly adjustable lenses for the z-deflection of the focal position along an optical axis of the eye. Such systems are for example described in US 2006/195076 A1 or US 2009/131921 A1. On the other hand, systems are also known in which the objective is slowly moved laterally, wherein a fast adjusting lens is used for the z-deflection of the focus along the optical axis of the eye. Such a system is described in DE10 2011 085 046 A1.

While in the initial development years of the LCS some application-related problems, in particular by introducing a liquid interface as a mechanical optical contact between the laser system and the eye were solved, see US 2012/0078241 A1 or U.S. Pat. No. 6,019,472, the integration of the technologies into a device, and to a lesser extent the integration of the technologies into a total workflow or a working environment were in the foreground. In particular, the cooperation between the femtosecond laser and the continued need for a surgical microscope during cataract surgery shows considerable deficits in the systems available on the market.

Most of the currently known systems are independent of the surgical microscope and, due to their size, often stand outside the operating theater later used for the actual implantation of the intraocular lens (IOL). A time-consuming repositioning and transferring of the patient is thereby usually necessary. This deficit was identified only recently and corresponding improvements were suggested:

In DE 10 2010 022 298 A1 and US 2012/316544 A1 it is suggested to couple the femtosecond laser directly and during the course of the surgery permanently with a surgical microscope. However, the required components according to the current state of the art are still too large for this, so that such a system would be too large during the IOL implantation phase, and therefore too restrictive and obstructive for the surgeon.

In WO 2008/098388 A1, a femtosecond laser is inserted under a surgical microscope if necessary, virtually between the surgical microscope and the patient, and is docked to the eye. Here, the surgical microscope and the femtosecond laser virtually operate sequentially and independently from each other. Above all, they are still separate devices.

Furthermore, a number of deficits regarding specific components have been shown in established systems, which negatively affect the quality of the surgery result, the efficiency in the implementation of the surgery or the risk minimization.

A micro objective scan as described in WO 2008/098388 A1 is indeed relatively time-efficient regarding the z-deflection for capsulotomy incisions, or for lens fragmentation as shown in DE 10 2011 085 046. Regarding access incisions, which not only provide a small-scale movement along the optical axis of the eye, but also a small lateral movement of the micro objective, as disclosed in US 2007/173794 A1, this solution is however very time consuming.

In addition, the incision guidance in systems with a fast z-deflection is time-critical for the capsulotomy. While a closed path in a lateral x/y plane does not present a problem for the capsulotomy in fast galvoscan systems, it is safety-critical in systems with a fast z-deflection, where the closing of the path only takes place after some time, and the eye can move during this period. Also with corneal access and auxiliary incisions, the advantage of a fast z-deflection of the laser beam does not take effect, as mainly long lateral paths also have to be covered here.

While the above points relate in particular to systems with pure micro objective scans, a number of improvements for systems with combined micro objective and mirror scan result. Combined scan systems are potentially superior compared to pure mirror scan systems with regard to the incision quality.

The contact elements or patient interfaces currently used are complicated in their handling, expensive to manufacture, have many error-prone components and are often unfavorably dimensioned.

Finally, the OCT signals in currently known systems are also disturbed by many reflections in the system. Furthermore, established OCT solutions also have many error-prone and slow components.

SUMMARY OF THE INVENTION

Example embodiments of the invention relate to systems and methods for short pulse laser eye surgery, with which the quality of the surgery result and the typical workflow can be improved, the efficiency of the surgery implementation and the safety of the surgery can be increased.

An example embodiment of a system comprises a short pulse laser system containing a short pulse laser source, a beam guidance device and an applicator head for directing a short pulse laser radiation from the short pulse laser source to the eye to be operated on. A short pulse laser source is thereby a laser source which emits the light not continuously but in a pulsed form. This means that the light is emitted in portions limited in time. The pulse rates of such a short pulse laser are usually in the femtosecond or picoseconds region. Pulse rates in the attosecond region are however also possible. By application of the pulsed light emission, very high energies can be realized, which are required for laser-tissue interactions via multiphoton absorption, as e.g. photodisruption or plasma induced photoablation. This is the case in all applications in which material is removed not only from the surface, but interactions are to be achieved in all three dimensions.

A beam guidance device ensures that the short pulse laser radiation emitted from the short pulse laser source is directed from the system in a provided manner to an exit location of the short pulse laser radiation. A beam guidance device can therefore for example be realized by an optical fiber or by a mirror system. It is also possible that the beam guidance means is realized by an entirety of these or similar components.

The applicator head which connects to the end of the beam guidance device opposite to the short pulse laser source forms the exit location of the short pulse laser radiation. It usually contains an optical system, such as an objective lens or, in a more complicated structure, an objective with several optical elements, in particular with several lenses.

It is advantageous if the short pulse laser system further has an x/y-deflection system, also called x/y scanning system, and a deflection system or scanning system for the z-direction and/or a lens system varying the divergence. The ability to deflect the short pulse of the laser radiation in the x-direction and in the y-direction and in the z-direction in a volume following the exit location of the short pulse laser radiation can also be realized by several deflection devices for respectively one direction, for example, a scanner for slow movement over a larger area and one for very fast for movement over a small area. Of particular interest are optimal solutions for the deflection in the z-direction.

The system for the short pulse laser eye surgery further comprises a surgical microscope with a tripod support and a microscope head. The microscope head contains the optical system of the surgical microscope. With such a surgical microscope, it is possible to obtain an optical overview of the state of the treatment at any time. However, the surgical microscope also contributes to an eye to be treated being aligned according to the system.

The system for the short pulse laser eye surgery also comprises a control unit, which is configured for the control of the system for implementing a short pulse laser eye surgery. The control unit can be designed in one piece or in several pieces. The components of the system for the short pulse laser eye surgery are advantageously connected to the control unit via communication paths. In the case of a multi-part design of the control unit, all components of the control unit advantageously connected to each other via communication paths. These communication paths can be realized by means of corresponding cables and/or also in a wireless manner.

Furthermore, the system for the short pulse laser eye surgery comprises a housing enclosing at least the short pulse laser source. A first and a second articulated arm, which are arranged on the housing or on an extension of the housing. An articulated arm comprises several joint members which can be moved mutually. The joint members are thereby arranged in such a manner that respectively two joint members are movably connected by at least one joint.

The microscope head is arranged on the first articulated arm, advantageously on the end of the articulated arm facing away from the housing. This articulated arm thus forms—together with the housing—the tripod of the surgical microscope. The applicator head is arranged on the second articulated arm, again advantageously on the end of the articulated arm facing away from the housing. The length of the second articulated arm on which the applicator head is mounted is advantageously designed so that the entire working range of the microscope head of the surgical microscope arranged on the first articulated arm can be used in a semicircle of about 180° before the system for short pulse laser eye surgery. Thereby, in particular the lengths of the joint members of the second articulated arm are designed correspondingly.

An interface between the applicator head and the microscope head is thereby provided with which the applicator head and the microscope head can be connected mechanically and optically and be released again.

The interface is in particular distinguished by a first structure on the first articulated arm and/or on the microscope head and a second structure on the second articulated arm and/or on the applicator head, which are either are matched according to the lock and key principle or can be connected via an adapter.

To connect the applicator head and the microscope head mechanically and optically with each other thereby means, in addition to the mechanical connection and thus the production of a solid relationship between the applicator head and the microscope head with each other, to connect both in such a manner that the imaging beam path of the surgical microscope passes through the applicator head. An optical path for the structures of the eye to be observed with the surgical microscope is thereby provided through the applicator head.

According to example embodiments of the invention, the beam guidance device for the short pulse laser radiation passes through the second articulated arm. The beam guide device is thereby configured in such a manner that it can follow all movements of the second articulated arm and can guide the short pulse laser radiation to its exit location on the applicator head in each position of the second articulated arm with the same quality.

Furthermore, according to example embodiments of the invention, the applicator head and the microscope head are movable both independently from each other and connected to each other in a three-dimensional volume. The mobility of the applicator head and the microscope head caused by their arrangement on the articulated arms in any arbitrary direction without any mechanical restriction of the three-dimensional volume caused by the system is therefore also given when the applicator head and the microscope head are connected to each other. This causes corresponding additional degrees of freedom in the first and second articulated arm. Because of the mobility of the applicator head alone, but especially connected to the microscope head, the exit location or the short pulse laser radiation is also movable in three-dimensional volume—in a preferred variant, also with respect to its beam direction at the exit location. It is thus also possible for example, to treat the patient not in the lying position, or while in a lying position, but with an engaged lying position.

With the present system for the short pulse laser eye surgery, not only the incision of tissue is thereby possible by means of plasma-induced tissue ablation and/or photodisruption-, but also the gluing of tissue by coagulation and a removal of tissue by ablative effects of the short pulse laser radiation can be achieved with such a system. Only the properties of the short pulse laser radiation must be adjusted according to the application objectives.

In an example arrangement, the inventive system for short pulse laser eye surgery further comprises an optical coherence tomography (OCT) module containing an OCT light source, an interferometer and a detector. The OCT module can thereby also be enclosed by the housing.

The system for short pulse laser eye surgery comprising an OCT module, which is optionally arranged for coupling a radiation emitted by the OCT light source into the microscope head or into the applicator head, has advantages. This can, for example, be achieved with the help of one or more optical switching points, which are provided in the beam path of the radiation emitted by the OCT light source and from a radiation from the OCT light source returning from an observation target in the eye. They can optionally be adjusted so that the OCT module can reach the observation target in the eye via the microscope head or via the applicator head.

The coupling of the radiation of the OCT light source via the applicator head has the advantage that it can be superposed with the therapeutic short pulse laser radiation in a simple and mechanically stable manner. Both beam paths can thus be calibrated to each other. This variant is therefore used in practice for the planning and control of the short pulse laser treatment.

The coupling of the radiation from the OCT light source via the microscope head in contrast enables the surgeon to carry out tomographic images of the patient's eye during and/or after the manual surgery phase. For example, intraocular lenses can be aligned precisely or free particles in the aqueous fluid can be identified and removed with the help of this technology.

Furthermore, it is technically advantageous to integrate a ring mirror for merging the short pulse laser radiation and the radiation emitted from the OCT light source radiation into the system for short pulse laser eye surgery. The merging thereby preferably takes place so that the short pulse laser beam is reflected by the ring mirror, while the short coherent radiation emitted by the OCT light source of the OCT module propagates through a hole in the ring mirror in the direction of the eye and the OCT detector detects the reflected radiation of the OCT light source from the eye through the hole in the ring mirror. The ring mirror may be movable for this. In one example embodiment, a 90° position of the coupling of the radiation emitted by the OCT light source into the beam path of the short pulse laser radiation exists, wherein the annular orifice is thereby arranged in a 45° position.

In another example embodiment for short pulse laser eye surgery, both the first articulated arm and the second articulated arm respectively have at least three joints.

When three joints are present, at least two of these three joints, or all three joints, may fulfill the function of a ball joint, i.e. offer not only a rotation possibility about a single axis. Such a joint must rather enable that a joint member can describe an arbitrary angle in the space to the adjacent joint member, which are both in a movable connection to each other by the joint, wherein the radius of action can possibly be restricted to a partial range of the space by other structural obstacles, but not to movement within a plane.

In another example embodiment, one of the three joints can have a single rotation axis. However, in the presence of only three joints, all three joints can fulfill the function of a ball joint. In this manner, the optimal mobility of the first and the second articulated arm which are both arranged on the housing or on an extension of the housing, is ensured both in the connected state and independently of each other in three-dimensional volume secured.

If, however, joints are used which respectively offer only one rotation possibility about an axis, a comparable mobility with at least five joints per articulated arm is realized, which have different rotation axes. Of these, three joints should enable the rotation about vertical axes and two joints the rotation about horizontal axes, i.e. represent tilt axes that lead to a tilting of the joint member following the joint.

In this example embodiment, —thus with the use of joints with respectively a rotation possibility about an axis—an articulated arm is advantageous having six joints with respectively one rotation axis per joint. In this case, three joints should enable the rotation about vertical axes and further three joints the rotation about horizontal axes. The tilting of the joint member following the joint or an end piece such as the applicator head or the microscope head is possible here.

In summary, the joints of each articulated arm shall for example realize six degrees of freedom, which are given by three vertical and three horizontal rotation axes, wherein vertical and horizontal rotation axes alternate along an articulated arm. In particular, a pair of a joint with a vertical rotation axis and a joint with a horizontal rotation axis, which are arranged in close proximity to each other, offers the same function as a ball joint.

Furthermore, the system for short pulse laser eye surgery preferably has a coupling position, which is encoded in the control unit in such a manner that a connection of the applicator head and of the microscope head takes place via the interface in a vertical position of the applicator head and the microscope head takes place, in order to avoid any mechanical tension. If the applicator head and the microscope head are connected via the interface, a further common tilting of these heads is then furthermore possible.

The system for short pulse laser eye surgery can, for example, be provided as a mobile system. It contains a device for transport for this. In particular, this can be designed as a roller system, so that the system for short pulse laser eye surgery can for example be moved manually or driven within a room or from one room to another. In an example embodiment, the roller system is supported by an electric motor, in order to move the possibly heavy system for short pulse laser eye surgery in a simple, precise and ergonomic manner.

In an advantageous embodiment of the system for short pulse laser eye surgery, the control unit is encoded for an automatic tracking of the position of the short pulse laser radiation in dependence on the position of the second articulated arm. This serves for the correction of positional deviations in particular of the focal point of a short pulse laser radiation by elastic deformations depending on the position of the second articulated arm and a given weight distribution in and at this second articulated arm, which contains the beam guidance device. The position of the articulated arm is thereby defined by the relative positions of the joint members to each other.

The tracking of the position of the short pulse laser radiation is thereby for example carried out automatically with respect to an adjusting position of the second articulated arm. The optical transmission of the short pulse laser radiation is aligned in this adjusting position, following this, the deviations of each position deviating from the adjusting position of the second articulated arm is determined and the respectively necessary correction for this position is set.

In a further advantageous embodiment of the system for short pulse laser eye surgery, the second articulated arm has at least one device for a weight balance independent from the first articulated arm.

During a surgical procedure, the second articulated arm on which the applicator head is arranged namely during the entire usage time of the short pulse laser system and, consequently, also of the applicator head with the first articulated arm, on which the microscope head is arranged, are connected. However, the second articulated arm has a relatively high weight: An applicator head may have a weight of several kilograms. This cannot be carried in a stable manner in every position by the first articulated arm. An independent counterbalance thus facilitates a high stability and flexibility of the movements. For applicative purposes, it may also be sensible to separate the microscope head from the applicator head during a treatment. In this case, both articulated arms also have to have a suitable weight balance, in order avoid uncontrolled and therefore unsafe movements of the system.

The weight balance thereby takes place with regard to a first tilt axis, thus a first joint enabling rotation about a horizontal axis. If necessary, a further weight balance can take place with regard to a further tilt axis.

The weight balance can for example be realized by a compression spring in spring arm member proceeding parallel to a joint member and accordingly movable in a parallel manner. A compression spring is contained therein, which pulls on a toothed belt, which is deflected into the parallel joint member via two toothed belt wheels.

Such a device for an independent weight balance of the second articulated arm containing a beam guidance means and carrying the applicator head as an exit location for short pulse laser radiation is a very advantageous version of the arrangement of the system for short pulse laser eye surgery. However, it is also advantageous for a short pulse laser system for eye surgery as described below, which comprises an articulated arm with the beam guidance device and an objective, in order to achieve a weight balance for any possible position of the articulated arm, so that the articulated arm, which also determines the exit location of the short pulse laser radiation from the short pulse laser system by its movement remains stable in any position and that optical location errors are kept low.

In a further arrangement, the system for short pulse laser eye surgery has a parking position and/or a transport position for the second articulated arm with the applicator head on the housing, which is adjusted to the geometry of the second articulated arm and/or the applicator head. For example, a structure on the applicator head and/or on the second articulated arm and a structure on the housing are also provided here, which are matched to each other according to the key-lock principle. This is for example supported by encoding a corresponding position of the applicator head determined by the movement of the second articulated arm, in the control unit of the system for short pulse laser eye surgery.

Alternatively, however, a parking position and/or a transport position on the housing is possible solely by encoding a corresponding position of the applicator head in the control unit of the system for short pulse laser eye surgery.

Regardless of the arrangement of the parking position and/or the transport position, in particular of the to reach into this, the parking position and/or the transport position is however characterized in that it indicates a position on the housing in which the applicator head is removed from the working range of an operator of the system, thus in particular of the physician, so far that a contamination by the operator from accidental contact with the components is unlikely and that the applicator head is protected as much as from collisions with other parts of the system but in particular with its surroundings. However, it is also advantageous if the parking position is not too far away from the working range of the operator, so that the coupling of the applicator head and of the microscope head can still be accomplished without major physical effort by the operator.

The parking position is further for example designed so that the applicator head is accessible insofar that a patient interface for fixing the position of an eye to the system for short pulse laser eye surgery can be coupled to the system for short pulse laser eye surgery without spatial obstructions.

For example, a mechanism to be switched by an operator or an automatically switched mechanism is provided in the system for short pulse laser eye surgery for releasing or connecting the interface between the applicator head and the microscope head. In a further example embodiment, the connection of the interface between the applicator head and the microscope head takes place by a bayonet closure.

Furthermore, adjustable elements may be provided on the first articulated arm and/or on the second articulated arm and/or on the applicator head and/or on the microscope head of the system for short pulse laser eye surgery, which elements enable a movement of the microscope head and/or the applicator head controlled by the control unit. Such adjustable elements can be realized by motors and/or other drive elements.

It is also advantageous if the beam guidance device passing through the second articulated arm of the system for implementing a short pulse laser eye surgery has a photonic crystal fiber with a hollow core. Such a photonic crystal fiber particularly fulfills the condition that the beam guidance means shall follow all movements of the second articulated arm and shall guide the short pulse laser radiation to their exit location on the applicator head with the same quality in any position of the second articulated arm.

Among the short pulse laser sources, femtosecond (fs) laser sources are by far the most commonly used laser sources are in eye surgery. They have proven to be particularly suitable and well controllable for these applications. Therefore, it is advantageous to also to use such a femtosecond laser source for a system for short pulse laser eye surgery.

The system for short pulse laser eye surgery for example contains a confocal detector. By recording an A-scan—that is, a one-dimensional scan along the optical axis—and/or a B-scan—a two-dimensional scan along the optical axis and vertical thereto—of two structures of an eye by application of an OCT module and of an intensity profile of the signal of the confocal detector when passing through the z-focal position of the short pulse laser radiation through the two structures, an offset and a scaling factor can be determined between the OCT signals and the intensity profile. This permits, as a result, to control the focal position of the short pulse laser radiation using OCT signals, in particular OCT images.

The coherence length of the OCT-light source in air is for example more than 45 mm, and according to another example embodiment is more than 60 mm. This makes it possible that the entire anterior chamber of an eye is detected in an A-scan, without having to adapt the optical path length of the reference beam path, even if the optical path to the eye changes through a lateral objective movement.

Example embodiments of the invention further include a method for positioning an applicator head and a microscope head in an above-described system for short pulse laser eye surgery. Such a method includes:

(a) The applicator head and the microscope head are first merging to an applicator microscope head unit and are connected to each other.
(b) The applicator microscope head unit is positioned over an eye to be operated on through free movement of the applicator microscope head unit in a three-dimensional volume.
(c) The applicator microscope head unit is lowered until the applicator head is in a predefined position above the eye and/or a patient interface releasably mounted to the applicator head has contact with the eye. Such a patient interface, which is also called "patient interface", can in particular be realized by a contact element, wherein a contact element is to be understood here as an overall term for different embodiments such as a liquid interface or a gel interface or a solid interface. The patient interface described below can be used here. If the patient interface has contact with the eye in this step, a releasable fixed connection between the eye and the patient interface is usually produced by means of a vacuum, thus by suction of the eye to the patient interface.
(d) The lens and/or the capsular bag and/or the cornea is processed by means of a focus of a short pulse laser radiation, thus for example a femtosecond (fs) laser.
(e) The applicator microscope head unit is raised again after the treatment.
(f) The applicator head of the applicator microscope head unit is placed in a parking position at the housing. In an example embodiment, the applicator head and/or the second articulated arm locks in this parking position and is held mechanically.
(g) The microscope head is separated from the applicator head. This for example takes place by an automatic releasing after a correct positioning in the parking position.
(h) The microscope head is positioned above the eye of the patient.
(i) Further surgery steps as e.g. the phacoemulsification and/or of the suction of the liquefied lens and/or of the insertion of the intraocular lens are carried out.
(j) The microscope head is placed into a position outside the surgical field or guided to the applicator head and connected therewith.

One such method is especially important in cataract surgery by application of short pulse laser radiation (LCS), as in a part of the surgical working steps of the focus of this laser radiation shall be directed into a tissue in the eye to be processed via the applicator head, however, at the same time an observation possibility by use of a surgical microscope is desired, and in another part of the surgical working steps only the surgical microscope alone is required, but at the same time freedom of work of above the eye to be treated is desired.

Another example embodiment of the invention includes a short pulse laser system for eye surgery that comprises a short pulse laser source which generates a short pulse laser radiation. In particular, a femtosecond (fs) laser source can be used at this point.

The short pulse laser system further comprises a lens system varying the divergence of the short pulse laser radiation which is generated by the short pulse laser source, and an x/y scanning system for the short pulse laser radiation.

The lens system varying the divergence of the short pulse laser radiation thereby contains at least a lens, but advantageously a system of different successive lenses in the beam path of the short pulse laser radiation, of which at least one lens can be adjusted in its position. This arrangement offers a possibility to focus the short pulse laser radiation and to displace the focus of the short pulse laser radiation in the z direction, that is, along the optical axis. By use of the lens system varying the divergence of the short pulse laser radiation a z-position of the short pulse laser radiation is also fixed in an eye to be treated.

The short pulse laser system finally comprises an articulated arm and an objective movable in the x- and y-directions, wherein the articulated arm inventively contains a beam guidance device. The beam guide device ensures that the short pulse laser radiation emitted from the short pulse laser source is directed from the system in a provided manner to an exit location of the short pulse laser radiation, here the objective movable in the x- and y-direction. The beam guidance device can also be realized through an entirety of different components.

The articulated arm with at least two joints, each fulfilling the function of a ball joint and contain at least two joint members, is movable. For example, it can be moved freely in a three-dimensional space. The object can also be adjusted in the z-direction in one arrangement.

In various embodiments of the short pulse laser system for eye surgery, the x/y scanning system contains an x/y mirror scanner or a gimbal-mounted mirror scanner or a mirror scanner for the x-direction with a downstream element for rotation about the optical axis. An x/y mirror scanner can thereby also comprise a separate x-scanner and y-scanner, which together act together as an x/y scanning system.

Advantageously, several scanners can also be provided for one direction, for example a scanner for a slow movement over a larger range and a scanner for a very fast movement over a small range. This is of particular interest in the z-direction, thus along the optical axis, preferably in combination with at least one lateral direction x or y.

Furthermore, a short pulse laser system for eye surgery can contain a patient interface which is used for fixing the position of an eye to a system for short pulse laser eye surgery. In one example arrangement, the patient interface comprises a contact element, wherein a contact element shall be understood here as an umbrella term for various embodiments such as a liquid interface or a gel interface or a solid interface. In particular, the short pulse laser system can contain a contact element according to the invention described below.

The field of view of the movable objective of the short pulse laser system for eye surgery is for example larger than 1.0 mm but smaller than 6.0 mm, in a further example larger than 1.5 mm but smaller than 3.0 mm. The field of view is hereby located in a field of view plane in which can be moved in the x- and/or y-direction through a scanning movement. The field of view plane itself can also be moved along the optical axis in the z-direction by a scanning movement. The cross section of the movable object depends in particular on the scanning range of the x/y scanning system. Thus the focus of the short pulse laser radiation can be placed in a targeted manner at any place of the three-dimensional scanning volume from the movable objective and from the mirror scanners through overlays of the beam deflections.

The optical system which is arranged in the beam path of the short pulse laser radiation, as well as the lens system varying the divergence of the short pulse laser radiation are preferably fastened on an optical system bench. The optical system bench itself is fastened with three points on, at or within a housing, at which the articulated arm is for example also arranged. All deformations of the fastening surface in the housing thereby have no influence on the state of adjustment of the optical system, but on the position of the optical system bench to enter the articulated arm with its beam guidance means. Changes to this position can be balanced with a beam stabilization.

An example arrangement of the short pulse laser system for eye surgery further comprises a system for the stabilization of a beam passage through the articulated arm, which includes a light source at one end of the articulated arm and a position-sensitive light sensor at the other end of the articulated arm.

The light coupling thereby takes place at an angle to the optical axis of the articulated arm, that is, that for example the light source does not sit on the optical axis, or that the light source sits on the optical axis, but does not radiate symmetrically in the direction of the optical axis.

This beam stabilization permits, despite different positions of the articulated arm, to position the deflection of the short pulse laser radiation in the x- and/or y-direction through the x/y-deflection system or the x/y scanning system for positioning the focus for example by an x/y-positioning of a movable objective accurately and to balance mechanical tolerances of the articulated arm and the alignment of the x/y-scanning system.

Example embodiments of the invention also include a method for incision guidance, especially in corneal eye tissue, by application of a short pulse laser system for eye surgery, in particular a short pulse laser system as described above, including the following steps:

(a) An objective of the short pulse laser system is positioned in the x- and y-direction, that is, vertical to the optical axis, such that at least a part of the x- and y-focal position of an incision pattern to be projected in a field of view plane are arranged within the field of view of the positioned objective. Thereby, the respective position of the focus of a short pulse laser radiation of the short pulse laser system in a three-dimensional processing volume in which a patient's eye can be treated, is determined by the focal position in the x- and z-direction.

(b) The focal positions of the incision pattern are, for example by a pulse of short pulse laser radiation through the objective fixed in its x- and y-position lens using an x/y scanning system and with a displacement of the focal position taking place after each x/y scan or parallel to the x/y scan in the z-direction imaged along the optical axis by application of a lens system varying the divergence and/or in the objective. An x/y scan is thereby a movement of the focus of the short pulse laser radiation in a lateral x/y plane. The energy of a pulse of the short pulse laser radiation in its focal point is selected so that a plasma-induced photoablation or photodisruption of the tissue is achieved. By an appropriate choice of the distance of the focal positions to be imaged, an incision is generated in the tissue in that effective ranges of the respective pulses of a focal position and a neighboring focal position at least contact, possibly partially overlap.

(c) The steps (a) and (b) are repeated for a further field of view, for which the objective is again positioned at another lateral position, until the entire incision pattern has been generated. The entire incision pattern was generated when all the focal positions of the incision pattern were imaged.

Another example embodiment includes a method for the incision guidance for the disintegration of an eye lens by means of a short pulse laser system for eye surgery, preferably a short pulse laser system as described above, which contains the following steps:

(a) The focal point of a short pulse laser radiation is positioned in a tissue of the eye lens to be processed, whereby a plasma-induced photoablation or photodisruption of the tissue of the eye lens is effected by a corresponding energy in the focal point of the short pulse laser radiation.

(b) An objective of the short pulse laser system undergoes a feed in the lateral direction in a first meridian plane of the eye lens by a length (L) with an overlay of an oscillating displacement of the focal point, having a main component along the optical axis, with an amplitude (A) for positioning further focal points of the short pulse laser radiation in a partial surface of the meridian plane. The oscillating displacement of the focus component can thereby also extend alone along the optical axis, thus only have one component along the optical axis. A meridian plane is understood to be an arbitrary plane extending parallel to the optical axis.

(c) The focal point of the short pulse laser radiation is displaced along the optical axis by a height (H), whereby the height (H) is selected so that, during a repetition of step (b), repositioned focal points of the short pulse laser radiation do not overlap with a previously positioned focal point.

(d) The steps (b) and (c) are again repeated in turn, wherein step (b) and step (c) can take place by reversing the direction of feed in the lateral direction and also along the optical axis, until focal points were positioned in the entire first median plane.

(e) The steps (b) through (d) are repeated for the positioning of focal points in a further meridian plane of the eye lens, until the eye lens is treated with focal points of the short pulse laser radiation in such a manner that the partial pieces resulting from plasma-induced photoablation or photodisruption do not exceed a maximum size. The maximum size is thereby determined by the suction possibilities and the size of the capsulorhexis or capsulotomy.

In the method for incision guidance for the disintegration of the eye lens, focal points of the short pulse laser radiation are for example only positioned during the movement of the focus of the short pulse laser radiation from the posterior to the anterior side of the eye lens, wherein again for example, the movement from the anterior to the posterior of the side of the lens is carried out faster than the movement from the posterior to the anterior side of the lens.

Alternatively, however, focal points of the short pulse laser radiation can be positioned over the entire oscillation cycle.

A distance of 10-50 μm is further for example kept during the positioning of focal points of the short pulse laser radiation of different median planes and different partial surfaces of a meridian plane.

The change of the meridian planes also preferably takes place in the area of the incision line of the meridian planes.

Embodiments of the invention also include a method for an incision guidance of a capsulotomy using a short pulse laser system for eye surgery, wherein an opening, in particular of the capsular bag, is generated in that focal points of a short pulse laser radiation are positioned in their x- and y-focal positions by application of an x/y scanning system, that in n steps from 1 to N, where N is a natural number larger than or equal 2, respectively a nth non-closed curve having a radius R and having a first and a second end region of a respectively rectified curvature as that of the non-closed curve results. The first end region of the nth non-closed curve has a first end region $R_{En1}$ and the second end region a second end region $R_{En2}$. The first end region radius $R_{En1}$ and the second end region radius $R_{En2}$ are thereby smaller than the radius R.

Furthermore, all end regions of the non-closed curves have an end each. The non-closed curves are thereby arranged to each other that for n of from 2 to N, the first end region of the nth non-closed curve intersects the second end region of the (n−1)th non-closed curve, and additionally the second end region of the Nth non-closed curve (that is, n is equal to N) the first end region of the first non-closed curve so that the ends of all end regions are arranged in the interior of a closed curve formed by the first to nth non-closed curve.

So that a corresponding incision results, the energy of a pulse of the short pulse laser radiation in its focal point is chosen so that a separation of the tissue of an eye is enabled by plasma-induced photoablation or photodisruption. Furthermore, the distance of focal positions is chosen so that the effective ranges, the so-called cavitation bubbles of the respective pulses of a focal position and an adjacent focal position contact at least, possibly partially overlap and thus enable a separation of the tissue in which an incision is produced by plasma-induced photoablation or photodisruption.

A superposition of an oscillating movement of the focal point along the optical axis with an amplitude (A) is thereby advantageous, so that variations in the z-direction, for example the position of the capsular bag, can be balanced.

With respect to the radius R, smaller deviations are possible between the radii R of the n non-closed curves.

In order to generate a closed curve with the aid of N non-closed curves, these N non-closed curves, which respectively have a first and a second end region, are arranged with regard to each other so that the first end region of the nth non-closed curve intersects the second end region of the (n−1)th non-closed curve and finally the second end region of the Nth non-closed curve intersects the first end region of the first non-closed curve, thus preferably from the second non-closed curve, the first end region of the non-closed curve to be generated is respectively generated over the second end region of the recently created non-closed curve that.

However, such a sequence of the handling of adjacent non-closed curves can be forgone and N non-closed curves can be generated so that after the generation of the last non-closed curve such a pattern as described herein has finally resulted and that a closed curve is present in summary.

A patient interface for fixing the position of an eye to a system for short pulse laser eye surgery also contributes to the solution. Such a patient interface comprises a contact element, but it can also be designed as a liquid interface.

The patient interface is manufactured in one piece and of a transparent or a partially transparent material. It contains a suction ring, a casing and an optical element at the top of the casing, wherein the upper side of the casing represents the side facing away from of the suction ring.

The suction ring is arranged on the side of the patient interface facing the eye and serves for the form-locking support and fixation of the patient interface on the eye of a patient.

The casing is preferably formed conically in the shape of a truncated cone. The lower diameter facing the eye, which can be used optically, should be at least 10 mm, for example larger than 13 mm and more for example larger than 14 mm.

The casing has at least one opening laterally, preferably two openings, to each of which a feed line is connected via a fixing aid, or which respectively permits the connection of a feed line.

The feed line or one of the feed lines permits the generation of a vacuum in the suction ring, for which the corresponding opening does not have to penetrate the entire thickness of the casing, but a connection to the suction ring is essential. A further feed line can permit the feeding of liquid into the patient interface, for which the corresponding opening penetrates an entire thickness of the casing. The feeding of liquid into the patient interface preferably takes place in such a manner that in a state in which the patient interface lies on an eye of a patient, the complete volume delimited by the eye, the casing and the optical element is filled with the liquid and the optical element is dipped into this liquid on its side facing the eye.

In one embodiment of the patient interface, a further suction structure of transparent material is provided in the contact element on the side of the casing facing away from the suction ring, and thus on the side of the casing facing away from the eye. This further suction structure serves for holding the contact element at an applicator head of a system for short pulse laser eye surgery, for example as described above, by a vacuum.

In a particular embodiment of the patient interface, the optical element is arranged in a tilted manner to the optical axis. Arranged in a tilted manner thereby means not arranged perpendicular to the optical axis. It is thereby possible that the entire optical element, or else only the surface of the optical element facing away from the eye is arranged in a tilted manner to the optical axis.

It is also advantageous if the surface of the optical element facing the eye which is contained in the contact element of the patient interface, has a hydrophilic coating or is surface-treated in a hydrophilic manner. Furthermore, it is advantageous if the surface of the optical element facing the eye is curved convexly. This serves to improve the wetting with a liquid, and thus in particular the prevention of bubble formation in the area of the optical element. Because of the convex shape of the surface of the optical element, bubbles that are possibly formed travel to the outer edge of the optical element, which is irrelevant for the optical imaging of the system.

Furthermore, it is advantageous if the surface of the optical element facing away from the eye, which is contained in the contact element of the patient interface has an anti-reflection coating. This serves to prevent the reflection of the incident laser radiation.

In particular, it is advantageous if the patient interface further comprises an applicator head protector. With this, the part of an applicator head facing the eye—with the exception of the optical system—can be covered when docking the patient interface to an applicator head of a system for short pulse laser eye surgery and thereby the sterility can be supported.

A patient interface with an applicator head protector having a recess which may be realized centrally in the applicator head protector is one option, and which further may be smaller than an upper casing diameter of the casing. This recess serves for implementing the optical system of the applicator head and its coupling to the optical element of the contact element.

According to a further example embodiment, in a patient interface that contains an applicator head protector, the contact element and applicator head are two separated or separable parts.

In an example arrangement, the applicator head protector of the patient interface has a mechanical coupling element. The mechanical coupling element is configured to connect the applicator head protector releasably to an applicator head of a system for short pulse laser eye surgery.

It is also a contemplated feature of the invention if the patient interface, in particular the casing of the contact element of the patient interface further contains an optical wave guide structure. The optical wave guide structure serves for the illumination by an additional light source, which is connectable to the optical wave guide structure, for example visible light with wavelengths between 350 nm and 780 nm, or in a further example light in the infrared range, in yet a further example with wavelengths between 781 nm to 1300 nm for the protection of the eye.

It is also contemplated that the contact element of the patient interface contains at least one marking. This is for example arranged casing area of the casing, thus near to the eye and serves for orientation and alignment.

Furthermore an optical unit of a short pulse laser system and a patient interface supports the solution of the above-mentioned object. In this inventive optical unit of a short pulse laser system and a patient interface, which contains a contact element with an optical element, the depth of field of an image in the coupled state as well as arranged in a direct succession, uncoupled state of the optical unit from the short pulse laser system and patient interface is, for example, at least 3 mm, for example larger than 5 mm. Preferably, the short pulse laser system is an above-described, inventive short pulse laser system and the patient interface is an above-described inventive patient interface. Due to the depth of field, reference structures of the eye and markings of the contact element of the patient interface can be detected sharply even in the undocked state, for example, with a camera. In the docked state of the eye, reference structures of the eye as well as incisions in the eye carried out by application of the short pulse laser system by the operator, particularly a physician, can be recognized well due to the depth of field.

The solution is further supported by a referencing method for relaxation and/or access incisions of a system for short pulse laser eye surgery, including the steps of:
  a) An image of the eye with reference structures is recorded by a camera in the state of patient interface not docked to a patient's eye, contains a contact element.
  b) The patient interface is docked within a few seconds to the eye.

The alignment of relaxation and/or access incisions by application of detection algorithms is implemented by application of recognition algorithms based on the reference structures and provided to the operator, in particular a physician, as information or therapy planning proposal.

The solution of the above-mentioned object is also supported by a referencing method for the orientation of a toric intraocular lens during its placement into an eye, in particular into the capsular bag of the eye after fragmentation and removal of a natural eye lens, including the steps of:
  a) A first image of an astigmatic eye is recorded using a diagnostic system for the detection of the steep and/or flat axis. The orientation of the steep and/or flat axis is stored along with the image, or is associated with the image. During this recording, the patient is usually in a seated position.
  b) A second image of the same astigmatic eye is generated with the patient interface docked, thus coupled, to the eye, or with a an undocked patient interface, which is however docked after that, and with the help of the system described here for short pulse laser eye surgery and compared with the first image. In the second image recording, the patient is usually in a lying position. By referencing algorithms, the orientation of the steep and/or flat astigmatic axis of the eye is transferred from the first image to the second image.
  c) After the laser treatment, and again with an undocked patient interface, a further referencing between the second and conducted the third image is implemented. In the third image recording, the patient is in a lying position. The eye structure has changed between the second and the third image, for example by light bleeding and/or redness on the sclera, wherein the orientation of the steep and/or flat axis of the astigmatic eye has remained the same.

d) Further images and video recordings of the eye are recorded during the alignment of the intraocular lens inserted into the eye referenced with the third image recording.

e) The intraocular lens is oriented with the help of a relationship established in previous steps. For this, an orientation aid is created for the physician in the surgical microscope.

Example embodiments of the invention also include a computer program product for encoding a control unit of a short pulse laser system for eye surgery for implementing and above-described methods, such as the method for the positioning of an applicator head the method for the incision guidance by application of a short pulse laser system for corneal eye surgery the method for the incision guidance for the disintegration of an eye lens by the application of a short pulse laser system for eye surgery the method for the incision guidance of a capsulotomy by application of a short pulse laser system for eye surgery the referencing method for relaxation and/or access incisions, the referencing method for the orientation of an intraocular lens.

The above summary is not intended to describe each illustrated embodiment or every implementation of the subject matter hereof. The figures and the detailed description that follow more particularly exemplify various embodiments.

BRIEF DESCRIPTION OF THE DRAWINGS

The present invention shall now be explained with reference to example embodiments. It shows:

FIG. 16: an x/y-projection of the focal points of a short pulse laser radiation in a first incision guidance of a short pulse laser system for performing the capsulotomy;

FIG. 17a: an x/y-projection of the focal points of a short pulse laser radiation in a second incision guidance of a short pulse laser system for performing the capsulotomy;

FIG. 17b: an x/y-projection of the focal points of a short pulse laser radiation in a third incision guidance of a short pulse laser system for performing the capsulotomy;

FIG. 17c: an x/y-projection of the focal points of a short pulse laser radiation in a fourth incision guidance of a short pulse laser system for performing the capsulotomy;

FIG. 20: a method for referencing the incision guidance in a short pulse laser system for eye surgery;

FIG. 21a: a third structure for referencing laser incisions with a patient interface at a short pulse laser system;

FIG. 21b: a fourth structure for referencing laser incisions with a patient interface at a short pulse laser system;

Figure 1:
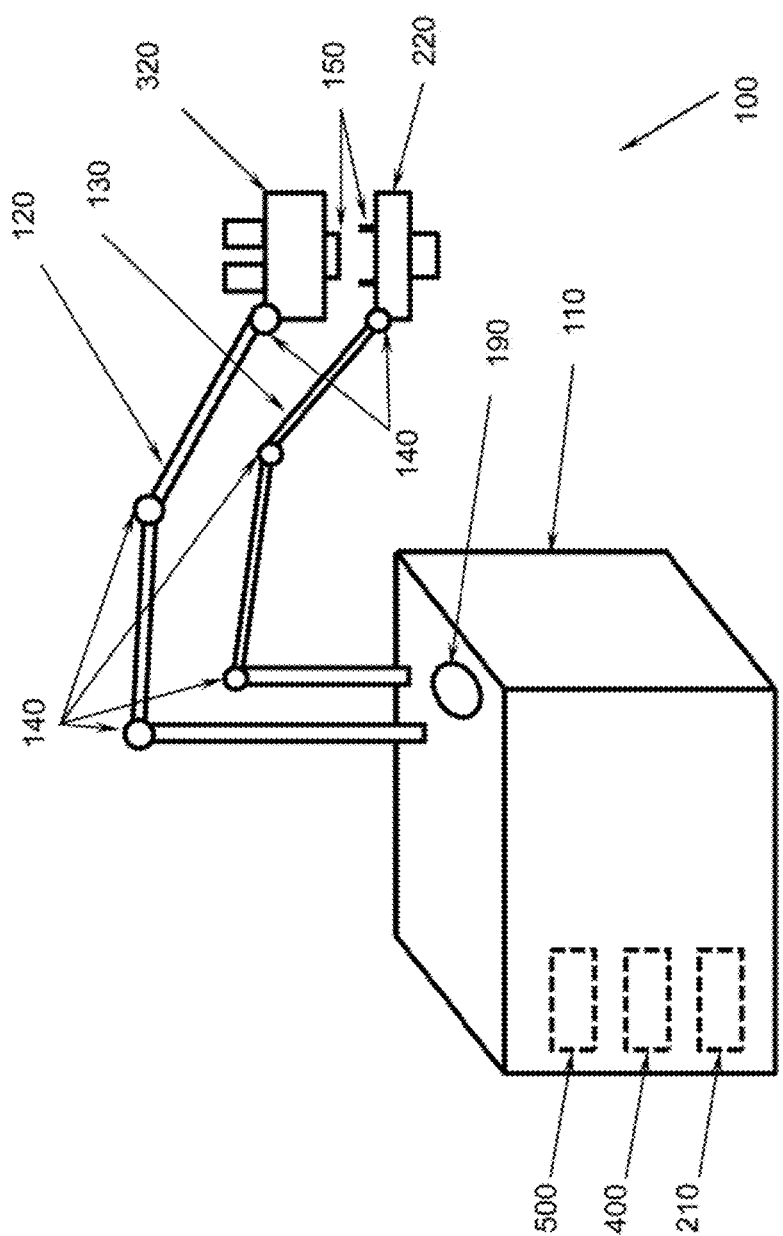
FIG. 1: a first system for short pulse laser eye surgery.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

In the following examples of a system for short pulse laser eye surgery, femtosecond lasers or fs lasers are used as short pulse lasers for a short pulse laser system and for the corresponding methods, which are the most commonly used short pulse lasers in the field of eye surgery by means of lasers—and therefore also the best understood. Nonetheless, all systems and methods described herein can also be implemented with other short pulse lasers. Fs lasers are thus, unless explicit reference is made to the pulse length as a differentiating characteristic, synonymous with short pulse lasers.

OCT, optical coherence tomography, is also referred to in the following. OCT is thereby, unless explicitly not differentiated regarding the different variants a synonym for all methods that measure distances in the eye using the by the optical short coherence or can detect images from the eye or its components, such as time domain optical coherence tomography (TD-OCT), spectrometer-based frequency domain OCT (FD-OCT) or wavelength sweeping-based swept source OCT (SS-OCT).

System Design of the Entire System and Workflow

Figure 2:
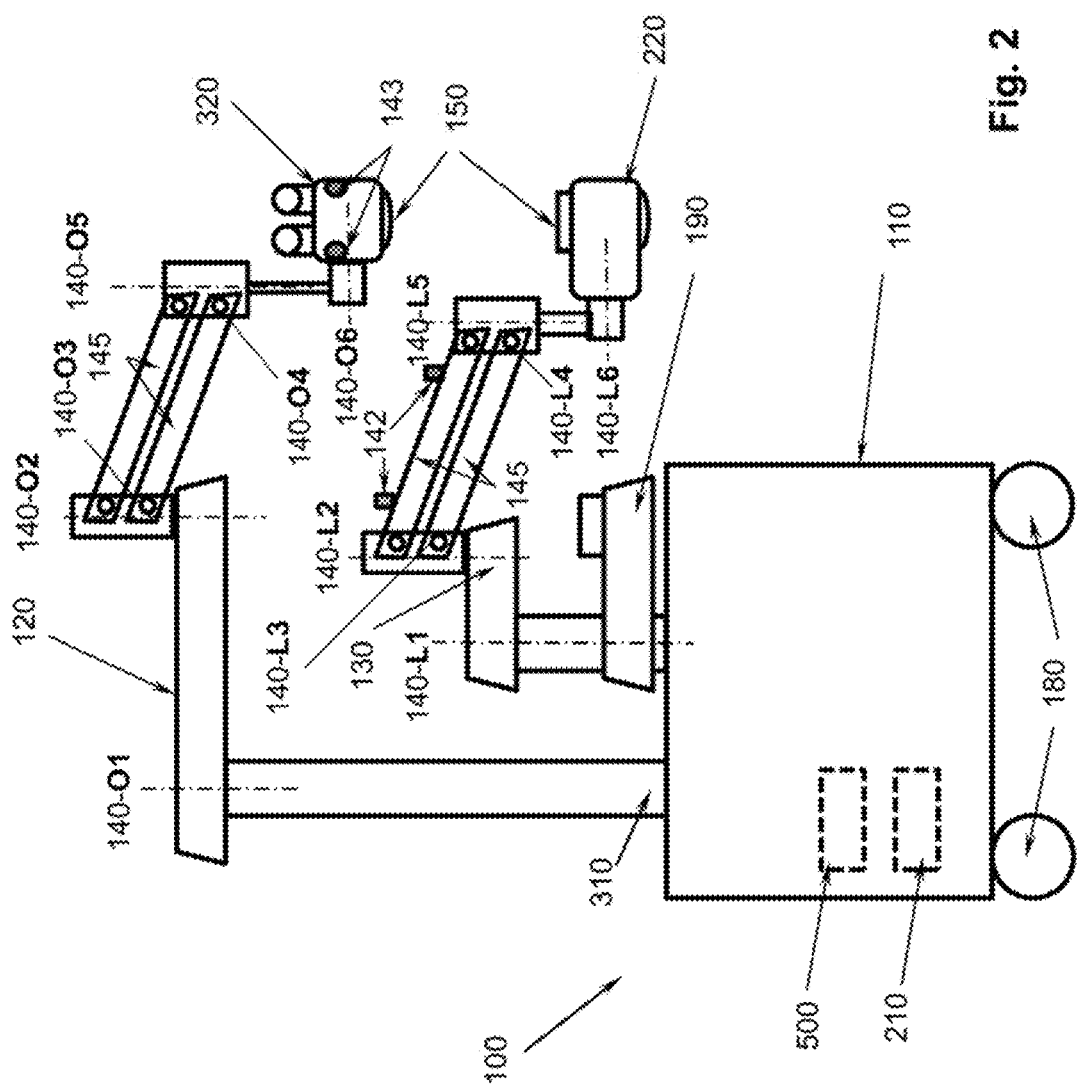
FIG. 2: a second system for short pulse laser eye surgery.

In order to improve the integration of the different components with respect to an optimized workflow and an optimized work environment for the operator, for example a physician, especially an eye surgeon, a structure of a first and a second system for short pulse laser eye surgery 100 is disclosed in FIG. 1 and in FIG. 2, which contains an fs laser system as a short pulse laser system 200 with a short pulse laser source 210, here thus an fs laser source, a beam guidance device 230 and an applicator head 220 for directing the fs laser radiation to the eye 900 to be operated on.

The structure of the first and the second system for the short pulse laser eye surgery 100 further comprises a surgical microscope 300 with a surgical microscope head 320. The entire surgical microscope and the optical system determining its function is thereby arranged in the microscope head 320.

The first system for short pulse laser eye surgery 100 of FIG. 1 further comprises the OCT module 400, which includes an OCT light source 405, an interferometer and a detector. The second system of FIG. 2 can also include such an OCT module in principle. For the cooperation of the system components shown in FIG. 1 and FIG. 2, the presence of an OCT module is however not mandatory.

The first and the second system for short pulse laser eye surgery of FIG. 1 and of FIG. 2 will be controlled by a common control device, that is, a control unit 500, which is either arranged centrally here or is distributed in several sub-units over the system. For this, communication paths between the control unit and individual components of the system or also between sub-units of the control unit can be used.

The systems for short pulse laser eye surgery 100 of FIGS. 1 and 2 further contain a housing 110, which may also be referred to as a console. This housing 110 encloses the fs laser source 210 and the control device as the central control unit 500, in the case of the first system of FIG. 1, the housing 110 also encloses the OCT module 400.

The microscope head 320 is attached to a first articulated arm 120 and the applicator head 220 is attached to a second, separate articulated arm 130, through which the light of the fs laser source 210 is supplied to the applicator head 220. For this, a beam guidance device 230 passes through the second articulated arm 130. The first articulated arm 120 and the second articulated arm 130 are mounted on the housing 110 or on an extension of the housing 110.

An interface 150 is provided at or in the vicinity of the applicator head 220 and of the microscope head 320, through which the applicator head 220 and the microscope head 320 can be connected with each other mechanically and optically.

For releasing or coupling the microscope head and the applicator head 220 with the help of the interface 150 a mechanism is provided to be switched by the physician or an automatically switched mechanism is provided.

The second articulated arm 130 contains the same degrees of freedom as the first articulated arm 120, which simultaneously forms the tripod of surgical microscope 300. The necessary degrees of freedom are generated by a corresponding number, arrangement and design of the joints 140 of the articulated arms 120 and 130, through which the applicator head 220 and the microscope head 320 are movable in a three-dimensional volume both independently of one another as well as connected to each other. In the case of the first system for short pulse laser eye surgery 100 of FIG. 1, this is achieved by the use of three joints 140 with a ball joint function.

In the second system for short pulse laser eye surgery 100 of FIG. 2, equivalent degrees of freedom as the three joints 140 with ball joint function through three joints for rotation about the vertical axes 140-O1, 140-O2, 140-O5 and 140-L1, 140-L2, 140-L5 and a parallel carrying arm 145, which represents an articulated member of the first or of the second articulated arm 120, 130 with horizontal rotary 140-O3, 140-O4 and 140-L3, 140-L4 for up and down movement, thus a tilting movement.

Figure 3:
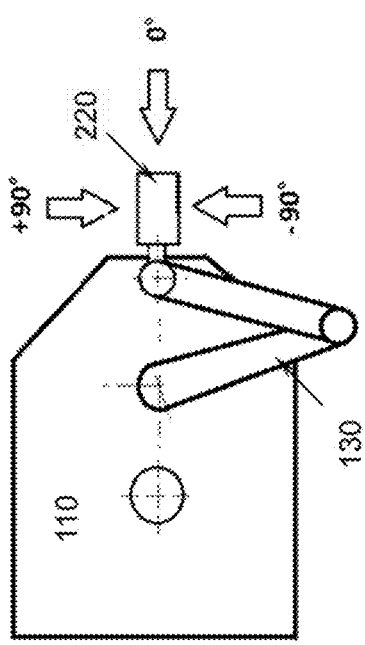
FIG. 3: the positions when connecting the applicator head and microscope head in plan view.

The first articulated arm 120 with the microscope head 320 additionally has a horizontal tilt axis for the inclination of the microscope head 140-O6. This can also be realized through the applicator head 220 for the coupling +/−90°, in that this is suspended rotatably on the horizontal axis 140-L6 of the last joint member is suspended. In the coupling position 0°, the surgical microscope head 320 can only be coupled in a vertical position. This is represented in FIG. 3, which shows the positions when connecting the applicator head 220 and microscope head 320. The thick arrow thereby shows the direction of view of the physician into the oculars of the surgical microscope head 320.

The surgical microscope head 320 thus has its own tilt axis 140-O6, which can be operated manually. In the coupling position +/−90°, this tilt angle can be balanced by an additional rotational axis 140-L6 in the applicator head 220. This is not possible in the coupling position 0°. Furthermore, it must be excluded implicitly that the operator, thus usually the physician, manually adjusts the tilt axis 140-O6 of the microscope head 320 after the coupling to the applicator head 220. The joints of the second articulated arm 130 could be deformed thereby, leading to deviations of the optical axis of the second articulated arm 130, in particular of the beam guidance device 230 contained therein, and thus to deviations of the position of the focus of the femtosecond laser radiation in the eye 900. This problem is solved by a motorization of the tilt axis 140-O6 of the microscope head 320. The operation is similar to the manual operation with a rotary knob laterally of the microscope head suspension. Before coupling, thus connecting the microscope head 320 and the applicator head 220 via the interface 150, it can be checked by the software whether the microscope head 320 is vertical. The operator receives a request to correct when there are deviations, or the microscope head 320 is automatically brought into a vertical position. During the laser treatment of the eye 900 of the patient, an actuation of the tilt axis 140-O6 can be prevented by the software.

The lengths of the joint members of the second articulated arm 130 of FIG. 2 are designed so that the entire working range of the surgical microscope head 320 can be used in a semicircle of 180° in front of the device, thus in front of the system for short pulse laser eye surgery 100. Because of the lengths of the joint members there are areas to the right and to the left of the device 100, which cannot be reached in the coupled state, thus, when the microscope head 320 and the applicator head 220 are connected. However, this is compensated in that the stored second articulated arm 130, on which the applicator head 220 is arranged, can be bent to the right or to the left as required. For this, the applicator head 220 is taken by hand from a parking tray on the parking arm 190, pivoted to the other side and stored again. The electrical locking of the parking tray is released with a switch on the applicator head 220 for this. In addition, two gripping knobs 142 are provided to avoid a dead-center position, at which the second articulated arm 130 can be guided through a dead-center position, in which its joint members are stretched in a plane. The gripping knobs 142 are preferably arranged at a joint member between the penultimate and the last joint 140 or between the penultimate and the last joint 140 with a respectively vertical rotation axis. In order to move the articulated arm 130 out of the dead-center position again, an operator grasps both gripping knobs 142 and swivels the articulated arm 130 in again thereby. The gripping knobs 142 can be coated in a sterile manner, with a corresponding coating being changed after each surgery, so that, also during the course of a surgery, the second articulated arm 130 can be grasped at the gripping knobs 142 after a surgery step if necessary without compromising the sterility.

The joint 140-L3 of the second articulated arm 130 on which the applicator head 220 is arranged lies higher in order to enable the passing of objects, e.g. through the surgery assistance under the second articulated arm 130. The height of the arrangement of the joint 140-L3 is selected so that the minimum distances for safety to the first articulated arm 120, on which the surgical microscope head 320 is arranged, are complied with. For rotation angles above 180°, there is a risk of a collision of the two articulated arms 120, 130. In order to exclude this, the rotation angle of the E-Box, as the joint 140-O1 of the first articulated arm 120 is restricted to +/−95° by a stop in the axis of the joint 140-O1. Despite this restriction, this is sufficient to achieve an extended, three-dimensional volume in front of the device 100 and consequently to place a patient roughly on a couch in front of the device 100 and to complete everything else by the movement of the articulated arms 120, 13. In this manner, one can operate with different position possibilities of patient and special preferences of the physician regarding the arrangement of the patient and the system for short pulse laser eye surgery 100 can also be considered.

The applicator head 220 is located between the patient and microscope head 320 and has to be designed in a very compact manner for this reason. The necessary actuators for displacing the focus of the femtosecond laser radiation in the z-direction, i.e., along the optical axis, in the eye 900 are very space-consuming and their accommodation in the applicator head 220 is therefore not sensible. These actuators are therefore arranged in the console, thus the housing 110, in front of the second articulated arm 130 carrying the applicator head 220. In order transmit the scanned focus generated there into the eye 900, relay objectives are necessary in each joint member of the second articulated arm 130. These objectives are afocal. A scanned focus results in each relay depending on the focal position. The numerical aperture must be as low as possible in order to avoid optical breakthroughs and thus power losses in the second articulated arm 130 or in the beam guidance device 230 passing through the second articulated arm 130. This requires long relay systems. The joint member lengths of the individual joint members of the second articulated arm 130 are adapted to the lengths of the relay systems.

High demands are made of the accuracy of the optical transmission of the laser beam from the optical system in the housing 110 into the applicator head 220, particularly in connection with the movement possibilities of the second articulated arm 130. During the adjustment, one must pay particular attention that the mechanical rotation axis and the axis of the laser beam do not deviate both in the angle and in the location. Each deviation leads to wobbling of the laser focus in the eye 900 during a movement of the second articulated arm 900. In addition, elastic deformations due to the heavy weight of the second articulated arm 130 and the applicator head 220 arranged thereon are to be expected, which are highly dependent on the position of the second articulated arm 130. Therefore, the adjustment of the second articulated arm 130 is only possible in one position. In any other position deviations are to be expected. These are balanced by an automatic beam tracking, which measures the deviations and readjusts the position of the laser beam. This correction takes place within certain limits, which are given by the geometry of and the adjusting ranges of the actuators. The free diameter of the optical system is dimensioned so that, during utilization of the adjusting range, no vignetting of the laser beam results. The necessary stiffness of the bearings and the parts of the second articulated arm 130 results from the possible adjustment range of the automatic beam tracking. Elastic deformations shall not exceed the possibilities of the beam tracking. The stiffness of the joint member between the joints 140-L1 and 140-L2 of the second articulated arm 130, which is strained the most, is achieved by a strong ribbing, a box-shaped design and additional steel plates on both sides of the joint member. Highly stiff slewing rings are used for the bearing, which are biased without play axially with two needle bearings and radially with one needle bearing. Alternatively, angular contact ball bearings are possible in the O-constellation with a large distance of the ball runway.

The second articulated arm 130 offers possibilities for passing electrical cables through, the OCT optical fiber 410 and the vacuum hoses for the suction of a patient interface 600 to the eye 900 of the patient as well as for the suction of the patient interface to the applicator head 220. At the junction of the joints 140-L2/140-L3 and 140-L4/L5-140 all cables are guided outside joints 140, in order to avoid too much strain of the cables against torsion. At the joint 140-L1, the cables are guided concentric to the optical system through the joint 140.

Depending on the embodiment variant a shelf 190 for the applicator head 220 is mounted on the housing 110 or a storage structure 190 matched to the geometry of the applicator head 220 is mounted.

Figure 4:
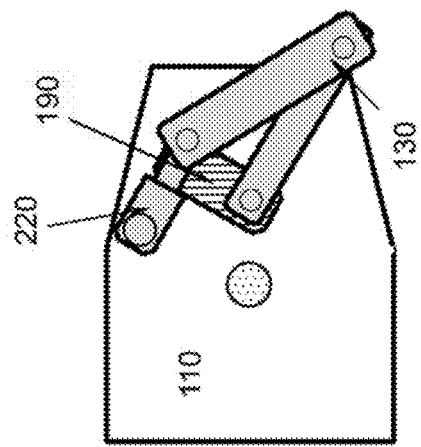
FIG. 4: the transport position of the articulated arm with applicator head in plan view.

For the transport, that is for example for driving the device 100 by use of a transport device 180 fixed under the device 180 through doors, the second articulated arm 130 and the applicator head 220 may not project laterally beyond the housing 110. This is achieved in that the applicator head 220, stored and locked in a parking tray, which is located on a parking arm 190, is pivoted into a position above the housing 110 and laterally backwards to the column of the surgical microscope 300, see FIG. 4. For this, the parking arm 190 also has to be pivoted about approximately 60°.

In order to bring the applicator head 220 into a resting or parking position, whose requirements differ from those of a transport position in that the projection of the second articulated arm 130 and the applicator head 220 over the housing 110 is less critical, the applicator head 220 is simply pivoted to the side and placed on the articulated arm. The locking of the transportation and parking position takes place for example with force-fitting detents.

The parking position preferably corresponds to a coupling position for connecting the microscope head 320 and the applicator head 220. However, it shall definitely enable a placement of a patient interface 600 on the applicator head 220. For this purpose, it is fully accessible from both sides. This is achieved by arranging a parking tray for storage and locking of the last joint member of the second articulated arm 130 in front of the applicator head 220.

The parking tray is rotatably mounted about +/−90° on a parking arm 190. The parking arm 190 is again rotatably mounted about 70° about the main axis 140-L1 of the second articulated arm 130. The parking tray is provided with detent positions for the parking position and the transport position. It contains an electromechanical locking mechanism for the articulated arm 130 of the applicator head 220, a force sensor and an inductive sensor for detecting the presence of the applicator head 220 or the last joint member in front of the applicator head 220 in the parking tray. The parking arm 190 and the parking tray are dimensioned so that the applicator head 220 overhangs in front of the device 100, is freely accessible from below for attaching the patient interface 600, and preferably at the same time the possibility exists to couple the microscope head 320 from both sides without hindrance. The length of the second articulated arm 130 at which the applicator head 220 is arranged, is dimensioned so that a coupled microscope head 320 also with an assistant microscope head cannot collide with the second articulated arm 130 and at the same time the minimum squeeze distances are observed.

In another embodiment variant, handles 143 with optionally sterile, exchangeable covers are attached to the microscope head 20 for positioning the microscope head 320. By the positioning of the microscope head 320 the applicator head 220 is also positioned when both are in the coupled state. The handles can be executed as switches for releasing electromagnetic brakes of the first articulated arm 120 on which the microscope head is disposed 320, be or as pure mechanical levers with friction brakes.

In a further example embodiment, elements adjustable via the control device 500 as e.g. motors are provided on the first and/or the second articulated arm 120, 130 or on the applicator head 200 or on the microscope head, which enable a movement of the microscope head 320 and/or the applicator head 220 controlled by the control device 500.

Spring elements are advantageously provided on one or both articulated arms 120, 130, which are coordinated so that the respective associated applicator head 220 or the microscope head 320 stays within a predetermined spatial area around the housing 110 and the surgical field without external forces.

The applicator head 220 weighs about 5 kg and cannot be carried by the surgical microscope 300 or the microscope head 320. The spring balancing of the first articulated arm 120, on which the microscope head 320 is arranged, is already used to capacity up to 1 kg with viewing oculars and possibly monitors. The second articulated arm 130, on which the applicator head 220 is arranged, thus contains a device for an independent weight balancing, as shown in FIG. 5.

Figure 5:
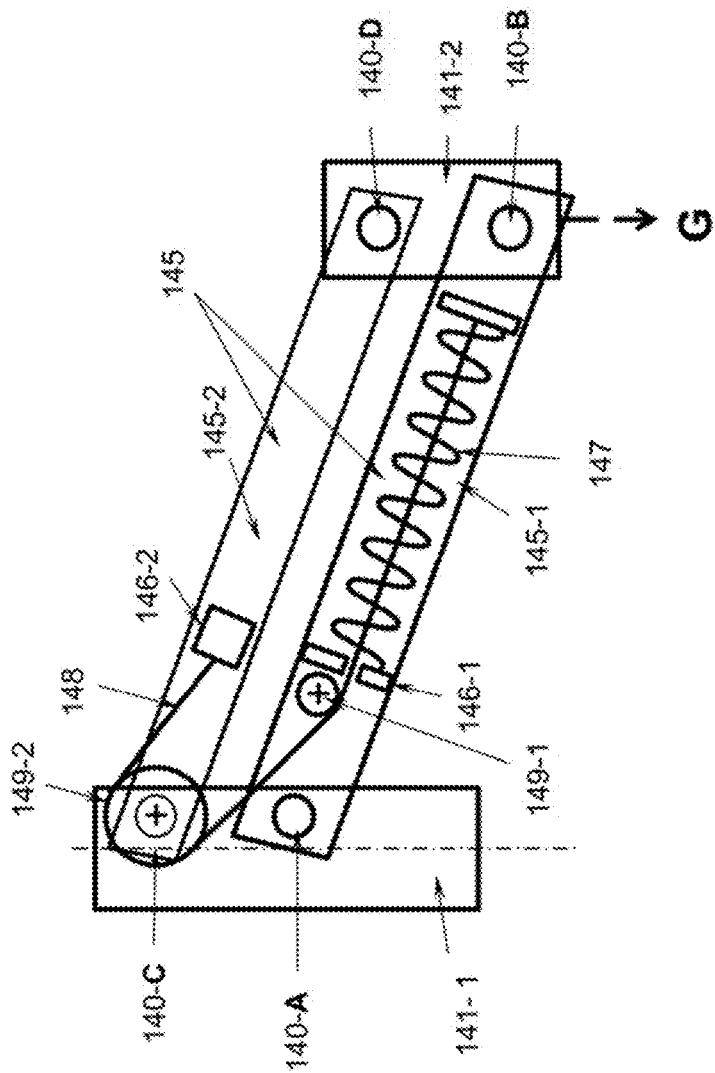
FIG. 5: a device for an independent weight compensation of an articulated arm.

The weight balancing for all masses to be balanced thereby takes place with respect to the joint 140-L3 (140-A in FIG. 5). The part of the second articulated arm 130 between the joints 140-L3 and 140-L4 (140-B in FIG. 5) is executed as a parallel support arm 145. The parallel support arm 145 consists mainly of four joints 140-A, 140-B, 140-C, 140-D and four joint members: the first rotary head 141-1, the second rotary head 141-2, the spring arm 145-1 and the stay 145-2. The weight balancing is realized by a compression spring 147 in the lower arm 145-1. The compression spring 147 pulls on a toothed belt 148, which is deflected into the stay 145-2 over two toothed belt wheels 149-1 and 149-2. There, the toothed belt 148 is suspended on a fastening 146-2. The compression spring 147 produces a moment about the joint 140-A, which is opposed by the moment generated by the weight G about point A and compensates this. The lever arm of the compensation moment is generated by the vertical spacing of the toothed belt 148 to the joint 140-A. This lever arm depends on the angular position of the spring arm 145-1. The spring constant of the compression spring 147 is dimensioned so that the position-dependent change of both moments is compensated. This ensures that in the weight compensation in the entire pivoting range lies within a predetermined tolerance range. The balanced weight force G is independent of the pivot position of the articulated arm 130 for the applicator head 220. Although the distance of the center of gravity changes to the pivot point 140-A by the pivoting of the applicator head 220, but this has no influence on the weight compensation. The moment changing thereby is supported by the stay 145-2, which is suspended in the pivot points 140-C and 140-D.

In an example embodiment, a video recording unit and an illumination unit are provided. These can alternatively be coupled into beam path to the or from the eye 900 via the applicator head 220 or the microscope head 320. In a specific embodiment, the second articulated arm 130, on which the applicator head.

In another example embodiment, the second articulated arm 130, on which the applicator head 220, is complemented by a photonic crystal fiber with a hollow core as beam guidance means 230. The fs-laser radiation is guided in the fiber within the hollow core and by periodic photonic structures analogous to a Bragg mirror. In this way, —similar to the free radiation—only a small pulse propagation takes place due to dispersion. Compared to a guidance through the second articulated arm 130 by a mirror system, the photonic crystal fiber has the advantage that it ensures a much more flexible laser beam guidance and reduces the complexity of the optical design. In this example embodiment, the second articulated arm 130 to which the applicator head 220 is mounted, serves, in principle, only for the mechanical holding of the applicator head 220, thus no longer influences the beam guidance through its structure itself.

Figure 6:
FIG. 6: a method for positioning an applicator head and a microscope head in a system for short pulse laser eye surgery.

The structure of a system for short pulse laser eye surgery 100 described herein supports method for the positioning of the applicator head and of the microscope head on the patient's eye illustrated below and with reference to FIG. 6, which contains the steps of:

(a) If the applicator head 220 and the microscope head 320 are separated, they are coupled by the operator, for example, the physician. For this purpose, the operator sets the microscope head 320 on the applicator head 220 at the interface 150, and actuates a lock; or a mechanism automatically leads to a lock when reaching the desired connection.

(b) The operator guides and positions the microscope head 320 over the eye 900 to be operated on. Thus, the applicator head 220 is also positioned over the eye 900.

(c) The operator looks through the ocular of the microscope head 320 and lowers the microscope head 320 and thus the applicator head 220, possibly with a further lateral alignment of the microscope head 320 on the eye 900, until the applicator head 220 is in a predefined position above the eye is 900 or a patient interface 600 mounted releasably on the applicator head, which contains a contact element 610 is in contact with the eye 900.

(d) The operator carries out the processing of an eye tissue 910, thus of the lens and/or the capsular bag and/or the cornea by application of fs laser.

(e) The operator lifts the microscope head 320 and thus also the applicator head 220.

(f) The operator brings the applicator head 220 into the parking position, hereby places the applicator head 320 on the shelf or the storage structure 190 at the housing 110 in one example embodiment.

(g) The operator releases the microscope head 320 from the applicator head 220 by the locking mechanism or the release occurs automatically when the correct positioning of the applicator head 220 the storage structure 190 is reached. As a result, the separation of the microscope head 320 from the applicator head 220 takes place.

(h) The operator positions the microscope head above the eye 900 of the patient.

(i) The operator carries out further incisions of the phacoemulsification and/or of the suction of the liquefied lens and the insertion of intraocular lens.

(j) The operator positions the microscope head 320 in a parking position away from the surgical field. In one example embodiment, the operator sets the microscope head on the applicator head, which is located on storage structure 190 on the device 100 and locks the locking mechanism or the locking mechanism is locked automatically when reaching the connection.

In an example embodiment of the method, the control device 500 calculates control commands for adjustable elements at the articulated arms 120, 130 and 220 or the applicator head and/or the microscope head 320 with the aid of obtained OCT images and/or video images, so that in particular, the steps (c) and/or (e), possibly all further steps, with the exception of step (i), are controlled automatically by the control unit 500.

In a further example embodiment of the method, once the microscope head 320 is locked with the applicator head 220, e.g. via a sensor, the device state is changed by the control unit 500. The fs laser can e.g. be switched on automatically and an illumination above the surgicalmicroscope 300 can be switched off. Accordingly, in the unlocked, that is, the separated state of the microscope head 320 and the applicator head 220, the fs laser can be switched off and an illumination above the surgical microscope 300 can be switched on.

Structurally, the housing 110, in particular the housing interior, is for example designed so that the components of the short pulse laser system 200, which are enclosed by the housing, thus the short pulse laser source 210 (here an fs-laser source) and optical components as part of the beam guidance means, can be displaced in the mounted state as a whole and on a container laterally over the column 310 of the surgical microscope 300. The column 310 thereby represents as an extension of the housing 110 a support structure for the first articulated arm 120, at which the microscope head 320 is arranged. The components of short pulse laser system 200 enclosed by the housing 110 are thus placed onto the footplate of the surgical microscope 300 in the mounted state and are fastened at four locations. In the second system for the short pulse laser eye surgery of FIG. 2, this takes place as close as possible to the wheels, which are fastened below the footplate as a transport device 180, as a rigid fastening with about 6 mm distance above the footplate.

To facilitate the stability of the optical adjustment of the components of the short pulse laser system 200 in the housing 110 and in the second search articulated arm 130, different arrangements are necessary. Elastic deformation of the supporting parts of the housing 110 by position changes of the first and/or second articulated arm 120, 130 must not affect the state of adjustment of the optical system between the fs laser source 210 and the entrance into the second articulated arm 130, on which the applicator head 220 arranged. These elastic deformations are not negligible especially when it is considered that the first articulated arm 120 with the microscope head 320 and the second link arm 130 with the applicator head 220, including the device for an independent weight balance in the form of a parallel support arm 145 and their structures respectively have a weight in the magnitude of 50 kg. During pivoting, center of gravity displacements result, which can lead to deformations in the range of several tenths of a millimeter. Elastic deformations of the second articulated arm 130, on which the applicator head 220 is arranged, or its joint members, are balanced by their own beam stabilization. Deformations of the optical system of the short pulse laser system 200 in the housing 110, thus before entering the second articulated arm, however cannot be balanced. The accuracy requirements of the console optical system, thus the optical system that is arranged in the housing 110 behind the short pulse laser source 210 and in front of the second articulated arm 130, however, are in the micrometer range and cannot be met without special constructive measures.

To comply with the requirements, the entire optical system of the short pulse laser system 200 located in the housing 110 prior to the entry of the second articulated arm in the beam path of the short pulse laser radiation including the output of the fs laser source 210 is arranged on an optical system bench on an optical bench or bolted thereto. The optical system bench itself is secured with three points on or at the housing 110. All deformations of the fastening surface of the housing thus have no influence on the state of adjustment of the parts on the optical system bench, but on the position of the optical system bench to enter the second articulated 130.

Figure 7:
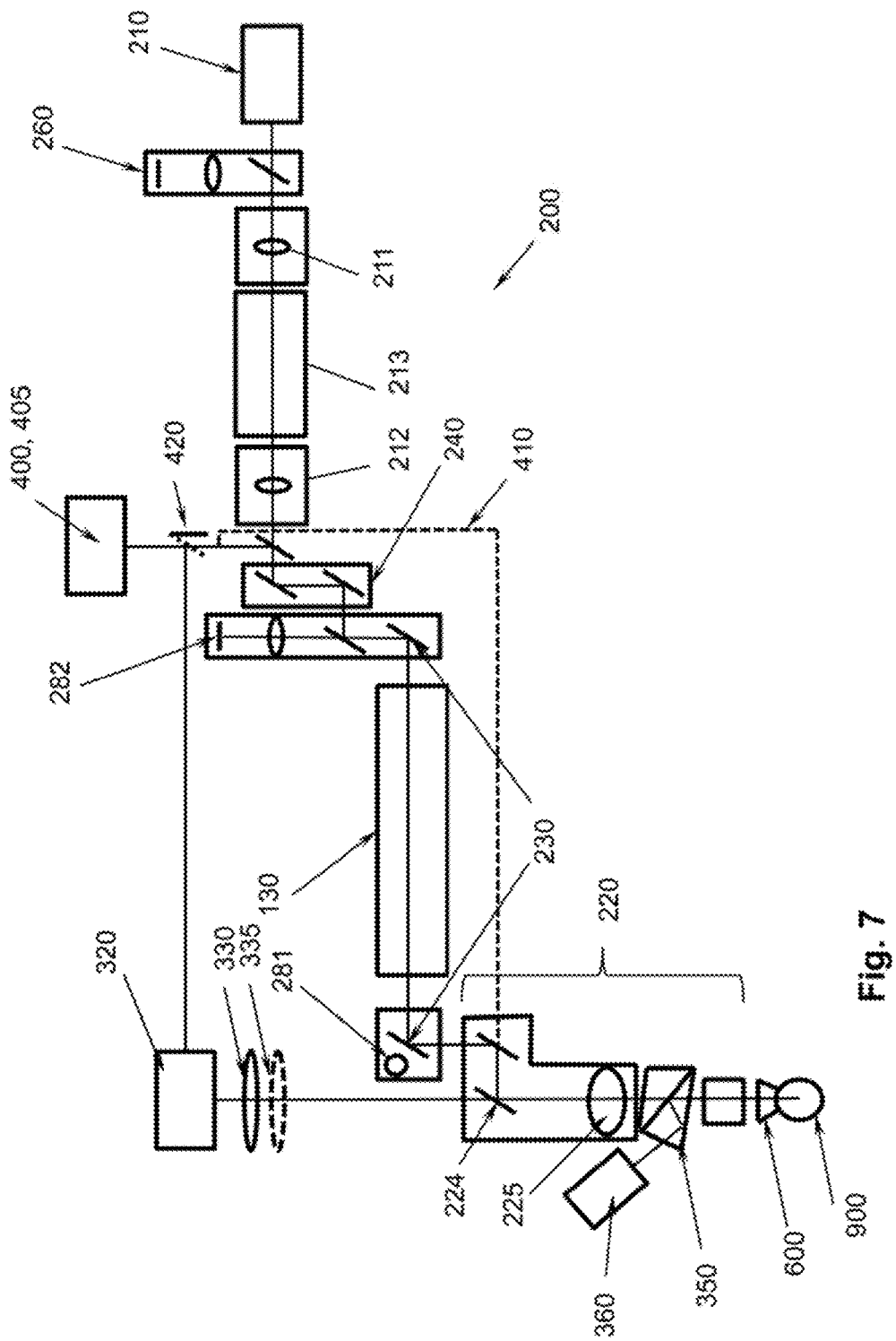
FIG. 7: a short pulse laser system for eye surgery (beam generation and optical system)

Changes of this position can be balanced by a beam stabilization with a system for stabilizing a beam passageway 280. A first active mirror of such a system for stabilizing a beam passageway 280 is located indirectly in the optical system bench. Another active mirror is located in the second articulated arm 130. Both form a beam walk. A laser diode 281 in the applicator head 220 emits a laser beam over all mirrors of the second articulated arm 130 including the mirror of the system for stabilizing a beam passageway 280 to two quadrant receivers 282 in the housing 110, which are fixed to the optical system bench. Deviations by deformations when moving the second articulated arm, or through movement of the optical system bench are recognized here and can be balanced by application of counter controls by use of the active mirrors. The optical system of such a system for stabilizing a beam passageway 280 is shown in FIG. 7.

As already described, the components of the short pulse laser system 200, which are enclosed by the housing, are for example fastened at four points as near as possible to the wheels 180 mounted to the footplate. The second articulated arm 130 as well as the electronics or the control unit 500 is also suspended indirectly therefrom. Alternating forces by pivoting the first articulated arm 120, on which the microscope head 320 is arranged or of the second articulated arm 130 on which the applicator head 220 is arranged, are transferred directly to the wheels 180 and the floor. The device 100 may not drive during a laser treatment. Changes in the force relations at the wheels 180 due to unevenness of the floor have a direct effect on the state of adjustment of the laser optical system. In the stationary operation, this influence will be balanced once before each surgery. The console is bolted at four points with the footplate of the surgical microscope 300. Two of the four points at which the components of the short pulse laser system 200 are bolted with the footplate can be adjusted in their height. Thereby, over determinancies arising from the fastening at four points can be balanced. Stresses due to expected unevennesses between the components of the short pulse laser system 200 mounted usually in and on a container and of the footplate of the surgical microscope 300 are avoided in that a distance of about 6 mm is produced between a bottom plate of the container and the footplate of the surgical microscope 300.

The container includes, for example, a base and cover plate, which are riveted with vertical walls to form a box. In comparison to a frame, in a compact size, transverse stresses can more easily be absorbed thereby. The container is firmly embedded in the housing 110: Components fastened on the container have therefore also a fixed relationship with the housing 110.

A cover plate separates the optical part above from electronic components and cables below. It is partially executed as a sandwich in order to guide the cables in intermediate spaces to the electronic components. The optical system bench with the output of the fs laser source 210 and the second articulated arm 130 is bolted to the cover plate. The plate-shaped construction of the container ensures sufficient stability for the optical system bench, but not for the second articulated arm 130, on which the applicator head 220 is arranged. In order to remain within the possibilities of the beam stabilization, the second articulated arm 130 fixed in a very stable manner. This is achieved by four rigid pillars directly under the screw points of the second articulated arm 130, which guide support forces directly into the base plate. The pillars will be charged only under pressure and can be realized by bending the walls twice, which usually consist of a metal sheet, can be realized. Buckling is prevented by skillful position of the bending edges.

The back of the container form parallel vertical walls, which both contribute to the stiffening of the container and serve for the accommodation of electronic components. The electronic components are vertical and parallel next to each other and can be pulled backwards out to the rear from the device 100 for servicing. A space for the cabling is reserved between the back wall of the device 100 and the electronic components.

The vertical arrangement results in a natural chimney effect for warm air, which can be used for the aeration. Therefore, openings are mounted in the vicinity of the electronic components, so that warm air from fans can be drawn pulled through the electronic components, and can be pushed out to the back. Thereby, a region of the room close to the surgery is largely spared by air movements that raise dust or can dry out the region near the surgery. The use of radial fans, that can be used to save space, is advantageous. A closed sheet metal plate is arranged above the fans, which separates the electronic components from the upper part of the device interior, in which components of the short-pulse laser system 200 are housed. The components of the short pulse laser system 200 are thereby largely shielded from the heat developing in the lower part.

System Structure of the Short Pulse Laser System: Beam Generating and Optical System In order to enable a time-optimized processing of the cornea in terms of access incisions and/or relaxation incisions, or incisions for processing the lens or a capsulotomy with an fs laser, the structure of a short pulse laser system shown in FIG. 7 is disclosed. FIG. 7 depicts an fs laser system 200 for eye surgery, especially for cataract surgery, which contains an fs laser light source 210. The light pulses of the pulsed laser radiation generated herein are guided into the eye 900 via a lens varying the divergence or a lens system 211 varying the divergence and further focus-adjusting optical elements 212, with which a controlled z-displacement of the focus of the pulsed laser radiation can be achieved, an x/y-mirror scanner 240 comprising an x-mirror scanner and a y-mirror scanners, or alternatively via gimbal-mounted mirror scanner or again alternatively via an x-mirror scanner with a downstream element for rotation about the optical axis, further a second articulated arm 130 contained over a mirror, an objective lens 225 movable in x/y direction and a patient interface 600 including a contact element and are focused in the eye 900.

Due to the lens varying the divergence or by the lens system 211 varying the divergence, which is changed along the optical axis—which corresponds to the z-axis—via an adjusting mechanism controlled by the control unit 500 in the position (its lenses to each other and to the optical axis), the divergence of the pulsed laser radiation and via other upper fixed optical elements such as a relay optical system 213, and/or movable focusing elements 212, the focusing position of the pulsed laser radiation is changed along the optical axis, that is in z-direction, in the eye 900.

By the x/y-movable lens 225, the lateral focusing position of the pulsed laser radiation is vertically set to the optical axis of the device, that is, in the x- and y-direction. Given the position of the x/y-mirror scanner 240, the femtosecond laser pulses are focused on a spot with a width of about 5 μm within which focuses the region of the eye 900 defined by the movement region of the movable objective 225.

During the scanning using the x/y-mirror scanner 240 and with an objective 225 remaining in a fixed position, the focal position of femtosecond laser pulses is displaced within the eye 900 within the image field of view of the objective 225.

With a simultaneous scanning by the x/y mirror scanner 240 and adjustment of the movable objective 225, a superimposition movement results.

In an example embodiment, a system for stabilizing a radiation passage 280 through the second articulated arm 130 is integrated into the short-pulse laser system 200 for eye surgery. As FIG. 7 shows, it comprises a light source 281 at one end of the second articulated arm 130, which couples its light in the second articulated arm with the help of the mirrors, which also guide and transfer the pulsed laser radiation as beam guidance means, and a position-sensitive position sensor 282 at the other end the second articulated arm. The light coupling takes place at an angle to the optical axis of the second articulated arm 130, that is, that e.g. the light source 281 is not arranged on the optical axis or, e.g. the light source 281 is arranged on the optical axis, but does not radiate symmetrically in the direction of the optical axis.

This beam stabilization allows, in spite of different positions of the second articulated arm, the deflection of the focus of short-pulse laser radiation by the x/y mirror scanner 240 of the x/y-positioning of the movable objective lens 225 in each direction x and/or y to accurately position and balance mechanical tolerances of the second articulated arm 130 and the mirror orientations.

For this, the steps of the following method are applied:

1. Determining the deposit position of the light beam of the light source 281 of a system for stabilizing a beam passage 280 on the position-sensor 282 with spatial resolution in front of a reference position or a reference angular position of the joint members of the second articulated arm 130. The deposit position depends on the rotation of the elements, that is, the joint members of the second articulated arm 130 to each other.

2. Calculation of the control magnitude to adjust the x/y-mirror scanner 240 for the focus positioning of the short-pulse laser radiation using the information for the storage position or storage positions of various positions of the second articulated arm 130. Essentially, the phase position of the swinging mirrors of the x/y-mirror scanner or the x/y swinging directions of a gimbal mirror are set. In an embodiment variant, if the storage positions exceed a predetermined value, the laser beam guidance on the eye 900 is interrupted or cancelled.

In addition, the arrangement already described above those of the optical system of the short pulse laser system 200, which is located in front of the second articulated arm 130 on an optical system bench is a measure to avoid the influences of mechanical deformation on the adjustment of the laser optical system.

In an example embodiment of the short pulse laser system 200 for eye surgery, the field of view of the objective 225 which is covered by the x/y mirror scanner 240, is larger than 1 mm in cross-section but smaller than 6 mm. In a another variant, it is larger than 1.5 mm but smaller than 3 mm.

A field of view which is too small causes that e.g. with laterally smaller incisions in the eye 900, the fast movement of the x/y scanner 240 alone is not sufficient, to carry out a complete incision. This has the consequence that the generation of the complete incision lasts considerably longer through the movement of the objective 225 through the then necessary slow method. The field magnitude of the objective 225 should therefore be chosen that that for example access incisions in the cornea 910 of an eye 900 with a length of about 1.5 mm in the x direction and during the incision into the depth of the corneal tissue 910, a projected y width of 2 mm do not need a movement of the objective 225, but only scanning with the scanning mirrors of the x/y-mirror scanner 240. However, the field of view should also not be too large, as otherwise the objective 225 becomes too heavy and thus will become too sluggish and slow for large-scale movements as e.g. during capsulotomy.

When coupling the microscope head 320 and the applicator head 220 via an interface 150, the beam path for the light to be received through the microscope head 320 passes through the applicator head 220. There are alternative embodiments to facilitate this:

In a first example embodiment, a laser optics in the applicator head 220 may be designed so that the mirror 224, whose role it is to deflect laser radiation coming from the fs laser source 210 to the objective 225 in the applicator head 220, has a partial transparency—particularly in the region of visible light, which is needed for the observation of the eye 900 with the microscope head 320, while the short pulse laser beam is reflected virtually completely. A further lens 335 for the adaptation of the radiation coming from the laser can thereby be arranged movably in front of the objective 330 of the microscope head 320 in the beam path of the surgical microscope 300.

In an alternative example embodiment, the laser optical system, which then contains a fully reflecting mirror 224, can be extended into the applicator head 220 by use of a slide. In order to utilize the microscope head 320 for observing the eye 900, the laser optical system is removed from the beam path of the surgical microscope 300, which passes through the applicator head 220. During the use of the short pulse laser radiation, the surgical microscope 300 cannot be used for observing the eye 900. To still create a possibility a possibility for the observation, the eye is 900 observed with light by a camera, for example an infrared camera 300 via a beam divider prism 350, for which the camera is sensitive, thus IR light here.

Optical Coherence Tomography and Navigation

To define the processing pattern in the eye 900, the structures of the eye 900, in particular the structures of the anterior chamber of the eye 900 are measured by optical coherence tomography (OCT). In the OCT imaging, the light of a short-coherence light source is scanned laterally over the eye 900, i.e. normal to the optical axis of the eye 900. Light reflected or scattered from the eye 900 is brought to interference with the light of a reference beam path. The interference signal measured by a detector is analyzed. From this, the axial distances of structures in the eye 900 can then be reconstructed. In conjunction with the lateral scanning, structures in the eye 900 can then be captured in a three-dimensional manner.

In order to determine an incision pattern in the eye 900 to be generated with the focus of a short pulse laser radiation, FIG. 7 shows the (optical) integration of an OCT module 400 in the configuration of a short pulse laser system for eye surgery 200 and, consequently also in a system for short pulse laser eye surgery 100.

In a variant of the structure, the same OCT-light source 405 is optionally coupled into the surgical microscope head 320 and into the applicator head 220. Accordingly, the reflected light of the OCT-light source 405 passes through the same interferometer with the superimposed reference light and detected by the same detector. This is illustrated in FIG. 7:

To improve the integration of the various components in an optimized workflow for the physician and to improve an optimized work environment, a structure is disclosed in FIG. 7, in which an fs laser source 210, an applicator head 220, a beam guidance means 230 (in FIG. 7 components of the beam guide means 230 are referred to only in an exemplary manner) for guiding the fs laser radiation into the applicator head 220 and from there to the eye to be operated 900 on, a microscope head 320, a movable second articulated arm 130 containing mirrors and an OCT module 400 containing a light source 405, a reference beam path, an interferometer, a detector and one or more switching points 420, controlled by a control device 500—not shown in FIG. 7—are controlled. The switching points 420 guide the light emitted from the OCT light source 405 and the light of the OCT-light source 405 returning from the eye 900 in a first state only via the applicator head 220 and in a second state only via the microscope head 320. This permits for example, the use of the OCT module together with the microscope head 320 for the surgery part of inserting the intraocular lens (IOL), in which the applicator head is not used and remains in a parking position decoupled from the microscope head 320 and ensures on the other hand that the illumination and detection beam path of the OCT module 400 for making the incisions by application of the focus of the fs laser radiation corresponds to the beam path of the fs-laser radiation, whereby alignment errors can be avoided. This is possible by the switching point or switching points 420, without having to integrate a further OCT module.

In order to improve the integration of the OCT module 400, FIG. 7 shows a short pulse laser system 200 for eye surgery containing an fs laser source 210 and an OCT module 400 containing a short coherence light source 405 and an interferometer, wherein the fs laser radiation and the radiation of the OCT short coherence light source 405 are fed to the applicator head 220 via the same second articulated arm 130 via the same articulated arm 130 containing mirrors and via this to the eye 900. After the merging of the radiation of both light sources, both are thereby laterally deflected via the same x/y mirror scanner 240. In this case, interferometer associated with the OCT module is arranged with a beam splitter and two mirrors in the beam path directly in front of the exit location on the objective 225 (not shown in FIG. 7).

This solution has the advantage that only a single beam guide device 230, here in the form of a guidance optical system formed with the aid of mirrors is necessary for the fs laser radiation and the radiation of the OCT light source 405 to the applicator head 130. Alternatively to the second articulated arm 130 containing mirrors, a photonic crystal fiber may be used as beam guidance device 230 for feeding the fs laser radiation and the radiation of the OCT short coherence source 405. In this case, the joint members of the second articulated arm 130 can be designed without mirrors.

In order to further improve the integration of the OCT module 400 and to offer alternatives, a further solution is also depicted in FIG. 7: The short pulse laser system 200 shown here also shows an fs laser source 210 and an OCT module 400 which contains a short coherence light source 405 and an interferometer, wherein the fs laser radiation is guided to an applicator head 220 via an x/y mirror scanner 240 for the lateral deflection and then via a second articulated arm 130 containing mirrors, the radiation of the OCT short coherence light source however is guided to the applicator head 220 via a optical wave guide fiber 410 without being guided over the x/y mirror scanner 240. The beam path of the fs laser and of the radiation from the OCT light source is thereby merged in the applicator head 220 and guided into the eye via a laterally movable objective 225.

This example embodiment has the advantage that none of the many optical elements of the second articulated arm 130 containing the mirror are arranged in the optical beam path OCT and thus their annoying reflections in the OCT detection signal no longer occur.

Figure 8:
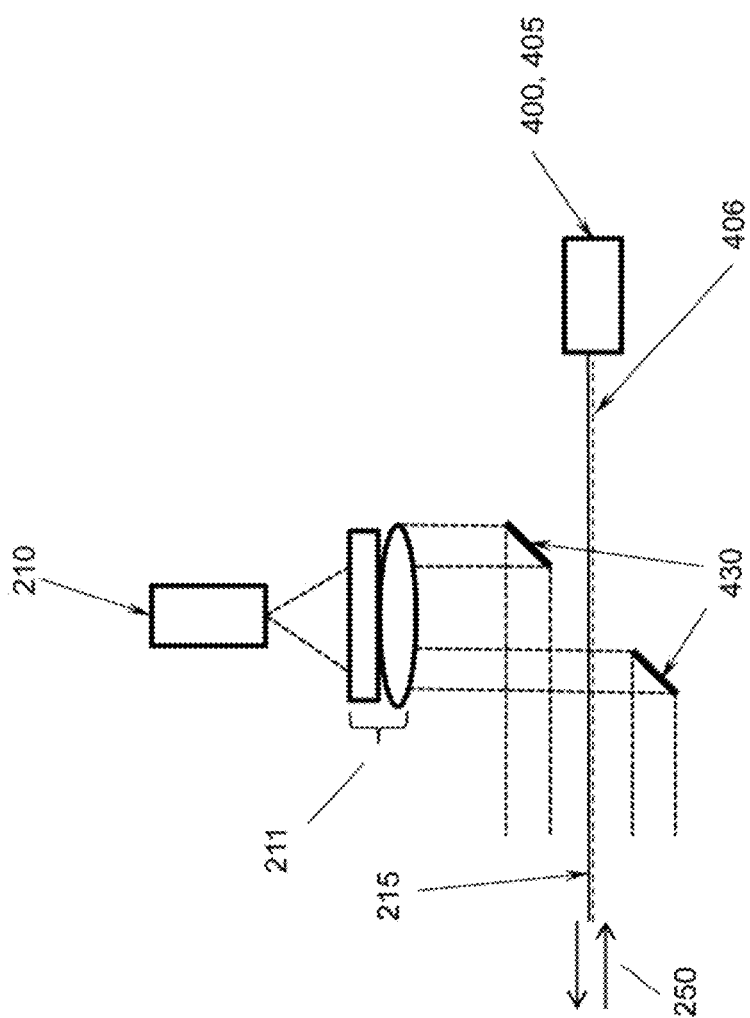
FIG. 8: a structure for the merging of short pulse laser radiation from the short pulse laser source and OCT radiation from the OCT light source.

For an integration of the OCT module 400 with an OCT short coherence light source 405 and an interferometer, FIG. 8 depicts a further detail, which enables merging of the radiation from a fs laser source 210 and from an OCT short coherence light source 405 of an OCT module 400 in a short pulse laser system on a common optical axis 215 and to follow a common optical beam path 250 to and from the eye 900. For this, the fs laser radiation coming from an fs laser source 210 on to a ring mirror 430 after a fs laser beam formation optical system 211 and is reflected on this in the direction of the eye 900 The radiation of the OCT short coherence light source 405 of the OCT module 400 however passes through a hole arranged centrally in the ring mirror 430 in the direction of the eye and thus on the same path as the fs laser radiation. Further, an OCT detector arranged in the OCT module 400 is detecting light coming from the eye via the hole in the ring mirror 430.

This has the advantage that mainly the high aperture regions are used for the forming of the fs laser radiation through the fs laser beam forming optical element 211. The focusing is improved thereby on the one hand. On the other hand, when focusing the fs laser radiation into the lens of an eye 900 during the further passage through the eye 900 in the region of the retina, only the peripheral regions are illuminated, whereby the risk for the patient of the damage in the central macula region is reduced. The ring aperture division further has the advantage that the radiation of the OCT short coherence light source 405, thus the OCT measuring and detection beam, is guided onto the optical axis 215 of the short pulse laser system 200 without an optical surface interfering because of reflections. This is not the case with a coupling by use of dichromatic filters or with virtually the same wavelength of the radiation of the OCT short coherence light source 405 and the fs laser radiation when coupling by application of a color-neutral divider. The color-neutral division would also lead to additional intensity losses for the radiation of the OCT short coherence light source 404 and for the fs laser radiation.

In a further embodiment not depicted here, the axis of the radiation of the OCT short coherence light source 405 is not identical to the optical axis 215 of the short pulse laser system 200, but has a small angle therewith. This has the advantage that further optical elements necessary for the beam formation of the fs laser radiation to the eye 900 do not reflect back OCT illumination light into the OCT detection beam path and thus affect the OCT signal.

In order to improve the accuracy of the calibration of the OCT imaging for positioning the focus of the pulsed laser radiation, FIG. 7 shows a confocal detector 260, whose focal aperture is located conjugated to the focal position of the fs laser radiation.

This confocal detector 260 permits also measuring structures of the eye when scanning the focus of the fs laser radiation in all spatial directions.

Figures 9A, 9B:
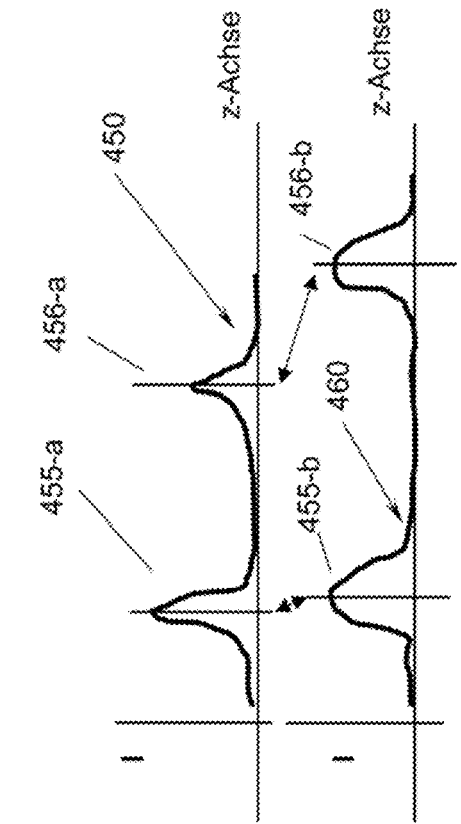
FIGS. 9a and 9b: the control of a short pulse laser system for eye surgery by means of signals from a confocal detector and an OCT module.

Thus, in a short pulse laser system, which contains a confocal detector 260 and an OCT detector in an OCT module, the following method of controlling the short pulse laser system for eye surgery can advantageously be carried out, also see FIGS. 9*a* and 9*b*.

a) Recording a B scan or an A scan 450 by application of an OCT module, which shows at least two structures 455-*a* and 456-*a* of the eye 900, e.g. of the cornea anterior and the cornea posterior.

b) Recording an intensity profile 460 of the signal of the confocal detector when passing through the z-focal position through the same two structures 455-*b* and 456-*b* of the eye 900, when illuminating the eye 900 through the fs laser radiation.

c) Calculating an offset and a scaling factor from the z-positions of the signals of the corresponding two structures obtained from the B or A scan and in the intensity profile.

d) Recording OCT images for setting the desired incision positions, setting the desired incision positions (by by reference to these OCT images).

e) Calculating and controlling the focus of the fs laser radiation using the OCT images and the desired incision positions and the offsets and the scaling factor.

By this method of controlling the short pulse laser system 200 it is enabled that the differences between the focal positions of the structures determined with the confocal detector 260, illuminated by the fs laser radiation or the same structures determined with the OCT module, e.g. by different wavelengths or different apertures, have no or only a slight effects on the control of the fs laser incisions and thus on the success of the surgery.

In order to improve the integration of the different components in a workflow optimized for an physician and an optimized work environment, a structure is further disclosed in FIG. 7, where a fs laser source 210, a beam guidance means 230 for guiding the fs laser radiation above the applicator head 220 on the eye 900 to be operated on and a swept source OCT module 400 containing an OCT light source 405 and an interferometer, will be controlled by a control device 500, which is not shown in FIG. 7. The applicator head 220 thereby contains a laterally scanning, movable objective 225. In one example embodiment, the coherence length of the OCT light source 405 in air is thereby larger than 45 mm, according to another example embodiment larger than 60 mm.

Because of the large coherence length of the OCT light source 405 it is possible that the entire anterior chamber section within an A scan given by the tuning of the swept source is detected, even when the optical path to the eye 900 extends or changes by the lateral objective movement, without the optical path length of the reference beam path has to be adapted e.g. by displacing a reference mirror.

Figure 10:
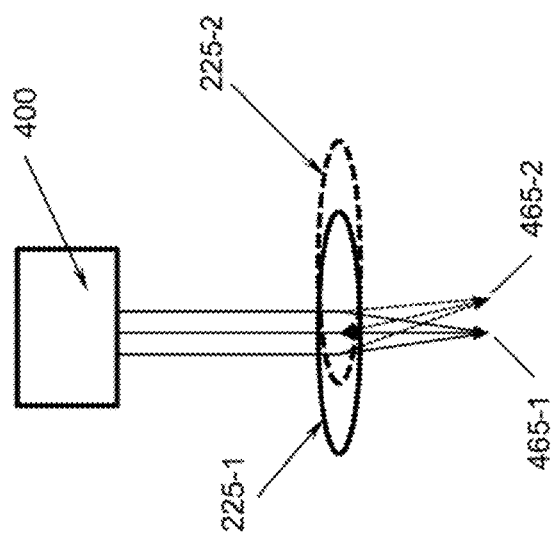
FIG. 10: the movement of the focus of the short pulse laser radiation with a laterally scanning objective of a short pulse laser system.

Such a change of the optical path length due to the objective movement is shown in FIG. 10. Between the objective positions 225-1 and 225-2 of the objective 225, the focus between positions 465-1 and 465-2 is displaced correspondingly, which coincides with a change of the optical path length of the OCT illumination beam path.

In order to balance the influence of the movement of the objective 225 on the OCT signal, the path length differences—typically up to 6 mm with different objective positions—are considered when calculating the A scan from the OCT signals. For this, when obtaining the A scans from the measured OCT signals, in a structure according to FIG. 7, the following steps are carried out in addition to other steps:

(1) Detection of the first OCT signals during the tuning of the OCT light source 405 at the objective position 225-1
(2) Detection of the second OCT signals during the tuning of the OCT light source 405 at the objective position 225-2
(3) Fourier transformation of the first OCT signals for obtaining the A scan; Fourier transformation of the second OCT signals multiplied with a phase factor depending on the relative position of the object position 225-2 to the objective position 225-1.

In order to balance the influence of the movement of the objective 225 on the OCT signal, in an alternative embodiment, the A scans obtained from the OCT signals are corrected by a position-dependent objective displacement along the measuring axis. For this, the following steps are carried out:

(1) Detection of the first OCT signals during the tuning of the OCT light source 405 at the objective position 225-1
(2) Detection of the second OCT signals during the tuning of the OCT light source 405 at the objective position 225-2
(3) Fourier transformation of the first OCT signals for obtaining a first A scan
(4) Fourier transformation of the second OCT signals for obtaining a second A scan
(5) Displacing the second A scan along the measuring axis by an amount depending on the relative position of the objective position 225-2 with respect to the objective position 225-1

Incision Guidance

Figures 11A, 11B:
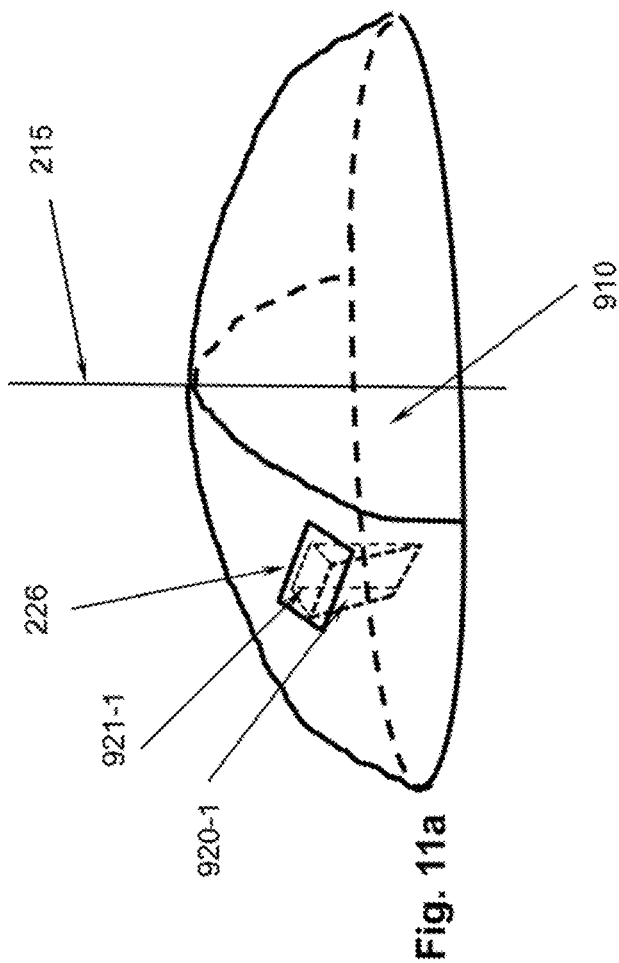
FIG. 11a: the incision layers in the tissue of an eye with a small field of the x/y-incision area projection.
FIG. 11b: a process for the focus shift of short pulse laser radiation in a short pulse laser system for eye surgery.

The above-described construction of the system for short pulse laser eye surgery 100 and of the short pulse laser system 200 supports the following method for the laser incision guidance, which is shown in FIGS. 11a and 11b:

If the incisions 920-1 to be executed in the tissue 910 of an eye 900 are in their focal positions 921-1, which are respectively projected on the x/y plane section, thus the incision 920-1, which is projected in an x/y plane is smaller than the field of view 226 of the objective 225, e.g. for small and steep access incisions, as shown in FIG. 11a, the following steps are selected for the method of the laser incision guidance, see also FIG. 11b:

(1) x/y-positioning of the objective 225, so that the x/y-focal positions to be projected, that is, the positions of the respective focus of fs laser radiation in x and y, are within the field of view 226.
(2) Projecting the focal positions of the incision pattern through the objective 225 fixed in its x/y-position using the x/y-scanning system, here thus the x/y-mirror scanner 240 optionally after each deflection of the focal position taking place after each x/y scan or parallel to the x/y scan by operation of the lens changing the divergence or the lens system 211 varying the divergence along the optical axis 215. This is will an example approach e.g. for small and steep access incisions.

Figures 12A, 12B:
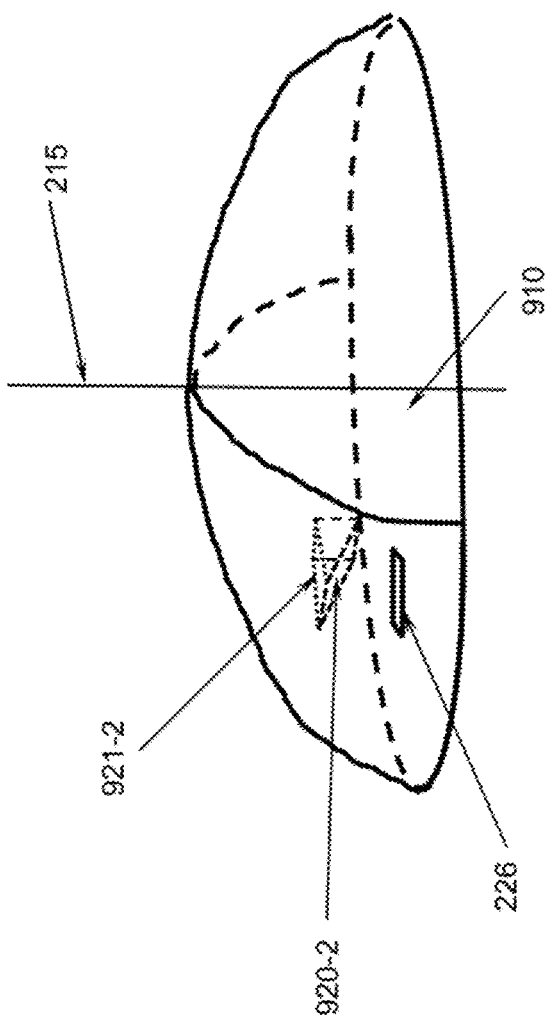
FIG. 12a: the incision layers in the tissue of an eye with a larger field of the x/y-incision area of the projection.
FIG. 12b: an alternative method for the focus shift of the short pulse laser radiation in a short pulse laser system for eye surgery.

If there is the necessity due to application reasons to implement larger incisions 920-2 or flatter incisions 920-2 perform with larger projected x and/or y extension than detectable simultaneously from the field of view 226 of the objective 225, see FIG. 12a, then the objective 225 can respectively be displaced so that the new field of views and the field of view 226 of the original objective position cover the entire incision area 920-2. For the respective new field of view, the still missing incision parts, can possibly be made up for by means of the x/y-scanning system, in this case 240, here thus the x/y-mirror scanner 240, possibly by changing the z-position of the focal position of the fs-laser radiation, be rescheduled. That is, one works with successively other lateral positions of the objective 225, until the entire incision 920-2 through the various sub-scanning has taken place. The x/y-mirror scanner 240 for the partial fields allow thereby to cover larger fields systematically and accurately in partial fields in a simple manner, particularly preferred square partial fields, by an incremental objective movement.

In the event that the incisions 920-2 lie very flat in the tissue 910, e.g. the cornea, i.e. the projected y-extension of the focal positions 921-2 of the incisions 920-2 projected in an x/y plane cannot be achieved completely with a y-scanner with a fixed objective 225 because the field of view 226 of the objective 225 is too small, while the incision length along the x axis lies within the field of view 226, then, alternatively to the above partial field scan, the following method can be chosen, see also FIG. 12b:

(1) simultaneous movement of the objective in the y-direction and movement of the lens or lens system for adjusting the z-focal position 211 and
(2) superposition of the fast x-mirror scanner movement.

If the incisions 920-2 are rather long and steep, thus have a large extension along the x-axis to a small extent in the y-direction, then it is accordingly advantageous to implement these incisions through simultaneous movement of the objective 225 along the x-axis and movement of the lens for the adjustment of the z-focal position 211 by superimposing the fast y-scanner movement.

Generalized to an incision 920-2, whose projected extension of the x and y extension which is, in focal positions 921-2 projected in an x/y plane larger in both x- and y-direction than the field of view 226 of the objective 225, this method can of course be applied in both directions.

While in the above description the z positioning means takes place by a lens varying the divergence or a lens system 211 varying the divergence, the above description of the incision applies generally for any type of z-focus adjustment, for example, even if the position of the z-focus takes place by positioning or movement of the lens 225 in the applicator head 220 along the optical axis 215.

Figure 13A:
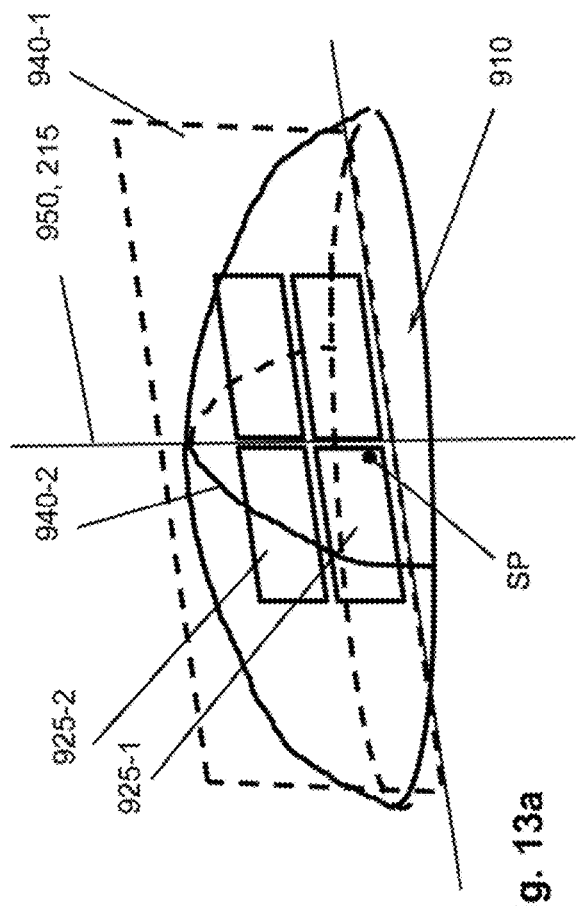
FIGS. 13a and 13b: the focus guidance of the focus of a short pulse laser radiation or the incision guidance by means of a short pulse laser radiation in the lens tissue of an eye.
Figure 13B:
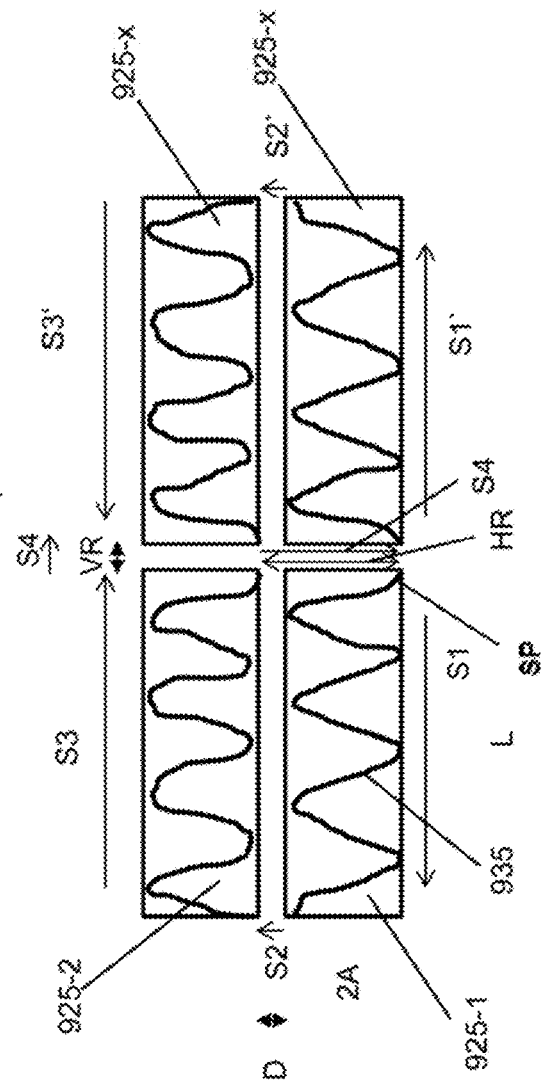

In order to set as few fs processing pulses as possible for the disintegration of the lens 910 and thereby to still enable that in the subsequent phacoemulsification no or only little ultrasonic energy has to be applied, a method and an incision pattern is shown is in FIGS. 13a and 13b, which weakens the lens 910 of an eye 900 in its structure. The method of the incision thereby comprises the following steps:

(S0) Positioning the focal point SP of a short pulse laser radiation, in the example of an fs laser radiation, in the lens 910 of an eye 900 to be processed. In one example embodiment, the focal point SP in the lens 910 is positioned with a safety distance to the posterior and anterior capsular bag of the eye 900.

(S1) Feeding the objective 225 in the radial direction in a meridian plane 940-1 of the lens 910 for a length L with superposition of an oscillating focus displacement 935 along the optical axis 215, 950 of both the fs laser system as well as of the eye with an amplitude A, wherein, in a first variant, only with the posterior to the anterior focus movement laser pulses are passed into the eye 900, and, in a second variant, laser pulses of the fs-laser radiation over the entire cycle. The meridian plane 940 of the lens 910 is thereby given by a plane passing through the center of the lens 910 in the vicinity of the optical axis 950 of the lens 910 or the optical axis 215 of the fs laser system 200 and proceeds approximately parallel to the optical axis 215, 950. Thus, an incision surface 925-1 is created. In a third variant, based on variant one, the anterior to posterior focus movement is performed faster, i.e. under a lower feed distance, thus less lateral movement than the feed distance at posterior to anterior focus movement. This results, with a constant laser pulse frequency, in that the laser pulses between two upward movements are laterally closer together and that incision surface 925-1 results.

(S2) Feeding of the focal point of the feed fs laser radiation along the optical axis 215, 950 by a height HR, wherein HR is selected so that the foci of the laser pulses set in the next step do not overlap with those foci of the laser pulses set in the previous step. In a variant, a distance D of 10-50 µm is kept between the laser foci of the two incision surfaces 925-1, 925-2. On the one hand, this positive distance enables that unnecessary incisions are not set in resulting cavitation bubble of the posterior section 925-1. On the other hand, no incisions are necessary distance region, because the bubble formation leads to a sufficiently large weakening in the tissue 910 and the two incision surfaces 925-1 and 925-2 possibly even merge together.

(S3) Repeating step S1 by reversing the feed direction in the radial direction and if necessary, step S2 (which is not necessary in FIG. 13b due to the size relations in this example). In one embodiment variant, these steps S1 and S2 are repeated until a safety distance to the posterior capsular bag is reached. In one variant, further supplementary steps are undertaken for the complete weakening of the lens, for example by simultaneous superimposed shifting of the laser focus deposit by means of a fast lateral scanner during the implementation of the steps S1 and S2.

(S4) Feeding of the focal point radially in the meridian plane 940 by a length of the VR and along the optical axis 215, 950 about the length HR, so that the incisions 925-x resulting in the following steps do not radially overlap with the preceding incisions 925-1, 925-2, etc. or have in one embodiment variant a radial distance D, with D for example between 10-50 µm. In FIG. 13b possible lengths VR and HR are given in an exemplary manner, but other lengths can also be selected as long as the incisions 925-x yet to be generated do not overlap preceding sections 925-1, 925-2, etc. Repeating steps S1-S4 (see S1 ', S2', S3') until the lens 910 is interspersed across the median plane 940 with incisions 925-1, 925-2, . . . 925-x, in an example embodiment, except for a minimum distance from the capsular bag and to the iris.

(S5) Positioning the focal point to the edge of another meridian plane 940-2. In an example embodiment variant, the change of meridian planes 940-1, 940-2, . . . takes place in the region of the incision line of the meridian planes 940-1, 940-2, . . .

(S6) Repeating steps S1-S6 until the entire lens 910 is interspersed with incisions 925-1, 925-2, . . . 925-x.

In addition to this incision pattern along the median planes 940-1, 940-2, . . . different overall incision patterns can be realized by the positioning of the basic-incision pattern of step (S1)-(S3). In this manner, lattice planes can also be realized, which are interspersed with incision surfaces. In all three-dimensional patterns at incisionsurfaces 925-1, 925-2, . . . 925-x, the degree of weakening of the lens cohesion can be adjusted via the distance of the incision surfaces 925-1, 925-2, . . . 925-x in connection with the bubble formation. Also, the distance of the incision 925-2 described in step S2 to the other comparable sections 925-1, 925-2, . . . 925-x according to step S2 in step in all can be adapted in all three spatial directions to the desired degree of weakening.

Figure 14A:
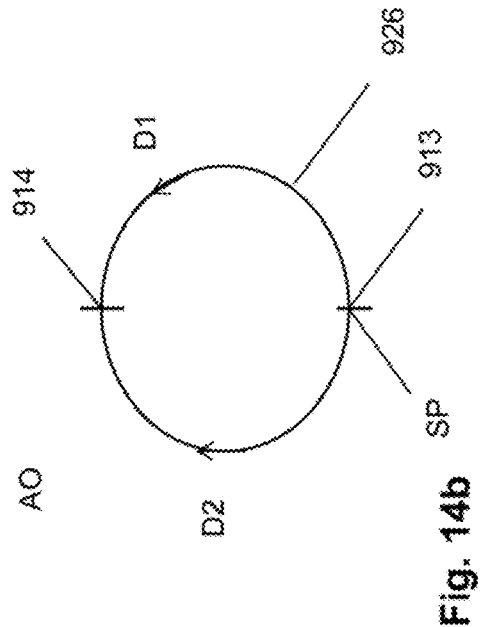
FIGS. 14a and 14b: the focus guidance of the focus of a short pulse laser radiation with an eye lens tilted with regard to the optical axis of the short pulse laser.
Figure 14B:
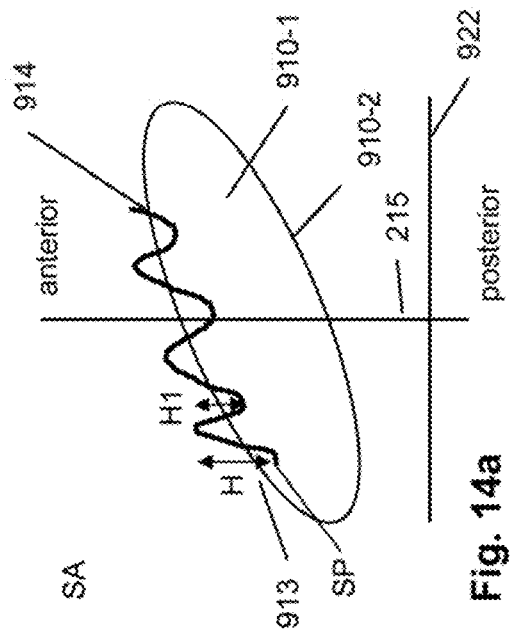

In order to permit an efficient cutting of the capsular bag 910-2 in capsulotomy for a fast z-scanning system, a method for the focus guidance with an inclined eye lens 910-1 in relation to the optical axis 215 of the laser system is shown in side view SA in FIG. 14a and in a plan view from above in FIG. 14b AO:

(1) Bringing the capsular bag 910-2 to be cut in an x/y/z-focal position SP, which gives a start position, behind the most posterior point 913 of the region of the capsular bag 910-2, which needs to be cut for the capsulotomy with the laser.

(2) Feeding the focal point or focus of the fs laser radiation along the z-axis 215 anterior by the distance H, while simultaneous feeding the focal point of the fs laser radiation in an x/y plane 922 along the edge of the capsulotomy 926 projected on the x/y plane 922 in direction D1, whereby the focal point, after passing through the distance H, lies anterior of the capsular bag 910-2.

(3) Feeding the focal point along the z-axis 215 posterior by altogether the distance H1 with simultaneous feeding the focal point in the x/y plane 922 along the path projected on the x/y plane 922 path in the direction D1, wherein H1 is less than H, and the focus lies posterior of the capsular bag 910-2 after passing through the distance H1.

(4) Repeating steps (2) and (3) until the most anterior point 914 of the region of the capsular bag 910-2, which is to be cut for the capsulotomy 926 with the pulsed fs laser radiation, has been reached.

(5) For the completion of the capsulotomy 926 the above steps are repeated while feeding the focal point of the fs laser radiation in the x/y plane 922 along the path projected in the x/y plane 922 in the opposite direction D2 (see FIG. 14b).

Figure 15:
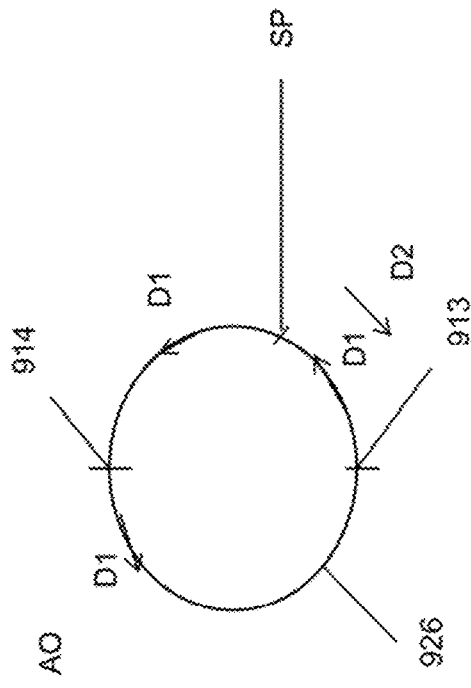
FIG. 15: the focus guidance of the focus of a short pulse laser radiation with an eye lens slightly tilted with regard to the optical axis of the short pulse laser.

For slightly inclined lenses 910-1 and the choice of a larger feeding in the x/y plane 922, the influence of the bubble formation of previous laser pulses on the pulse to be applied can be neglected. Then the following sequence of steps is advantageous, see FIG. 15 as a top view of AO:
(1) Bringing the capsular bag 910-2 to be cut in an x/y/z-focal position SP posterior to the location of the region 926 of the capsular bag, which needs to be cut for the capsulotomy with the laser.
(2) Feeding the focal point of the fs laser radiation along the z-axis anterior by altogether the distance H with simultaneous feeding the focal point in the x/y plane 922 along the edge of the capsulotomy 926 projected on the x/y plane 922 in direction D1, whereby the focal point, after passing through the distance H, lies anterior of the capsular bag 910-2.
(3) Feeding the focal point along the z-axis 215 posterior by altogether the distance H1 with simultaneous feeding the focal point in the x/y plane 922 along the path of the capsulotomy 926 projected on the x/y plane 922 path in the direction D1, wherein H1 is less than H in a first example embodiment, and the focal point lies posterior of the capsular bag 910-2 after passing through the distance H1.
(4) Repeating steps (2) and (3) until the most anterior point 914 of the region 926 of the capsular bag 910-2, which is to be cut for the capsulotomy 926 with the laser, has been reached.
(5) Repeating steps (2) and (3) while maintaining the feeding in the x/y plane 922 in direction D1, wherein, in the first example embodiment H1 is however larger than H, and until the most posterior point 913 of the region 926 of the capsular bag 910-2 is reached, which is to be cut with the laser.
(6) Repeating steps (2) and (3) while maintaining the feeding in the x/y plane 922 in direction D1, wherein, in the first example embodiment H1 is however now smaller than H, and until the capsulotomy 926 is closed in point SP.

In a second example embodiment, with slightly inclined lenses 910-1 and the choice of a larger feeding in the x/y plane 922, the incision path of the capsulotomy 926 can be passed through in the opposite direction D2. Also see FIG. 15:
(1) Bringing the capsular bag 910-2 to be cut in an x/y/z-focal position SP posterior to the location of the region 926 of the capsular bag, which needs to be cut for the capsulotomy with the laser.
(2) Feeding the focus of the fs laser radiation or another short pulse laser radiation along the z-axis 215 anterior by altogether the distance H with simultaneous feeding the focal point in the x/y plane 922 along the edge of the capsulotomy 926 projected on the x/y plane 922 in direction D2, whereby the focal point, after passing through the distance H, lies anterior of the capsular bag 910-2.
(3) Feeding the focal point along the z-axis 215 posterior by altogether the distance H1 with simultaneous feeding the focal point in the x/y plane 922 along the path of the capsulotomy 926 projected on the x/y plane 922 path in the direction D2, wherein H1 is larger than H, and the focal point lies posterior of the capsular bag 910-2 after passing through the distance H1.
(4) Repeating steps (2) and (3) until the most posterior location 913 of the region 926 of the capsular bag, which is to be cut for the capsulotomy 926 with the laser, has been reached.
(5) Repeating steps (2) and (3) while maintaining the feeding in the x/y plane 922 in direction D2, wherein, in the second embodiment variant H1 is however smaller than H, and until the most anterior location 914 of the region 926 of the capsular bag 910-2 is reached, which is to be cut with the laser.
(6) Repeating steps (2) and (3) while maintaining the feeding in the x/y plane 922 in direction D2, wherein H1 is again however now larger than H, and until the capsulotomy 926 is closed in point SP.

With inclined lenses 910-1 and with lenses 910-1 vertical relative to the axis 215, the cutting of the capsulotomy 926 with fs laser systems 200 with a fast z-scan, i.e. a speed of the z-focus deflection larger than or comparable to the speed of the x/y focus deflection, can take some time, so that the relative movement of the eye 900 changes with respect to the optical axis 215 of the laser system. The following steps of a method for laser focus control with a capsulotomy 926, see also FIG. 16 as a view from above AO, enable even with slight movements of the capsular bag 910-2 in the x/y plane 922, but also in the z-axis 215, that a capsular bag segment still separated completely from the rest of the capsular bag 910-2 results:
(1) Positioning the focus of the femtosecond laser radiation in the x/y plane 922, and with respect to the z-position in the vicinity of the capsular bag 910-2.
(2) Guiding the focal point or focal point in the x/y plane 922, along the edge of the area the capsular bag 910-2, which needs to be cut, in a first section A1 with a first radius R1.
(3) Guiding the focus in the x/y plane in a second section A2 with a second radius R2.
(4) Guiding the focus in the x/y plane 922 in a third section A3 with a third radius R3, wherein the first radius R1 and the third radius R3 is smaller than the second radius R2, such that the path of the focal point, which is results by the setting of individual pulses cuts through the first section A1 or the second section A2.

Thereby, in steps 2, 3 and 4, the z-position of the focus of the femtosecond laser radiation is changed in an oscillating manner with such a large oscillation amplitude, that the laser pulses set during the oscillations cut through the capsular bag 910-2 by photodisruption processes.

In steps 2, 3 and 4, simultaneously to the guidance of the focus in the x/y plane 922 also in an oscillating manner, at least once, for example several times, in another example more than five times, the z focal position is changed periodically for each of the sections A1, A2 and A3.

In systems with fast x/y scanning systems 240 for cutting the capsulotomy 926, that is, x/y scanning systems 240, whose speed of the x/y-focus deflection is larger than the speed the z-focus deflection, the problem of meeting the third section A3 of the capsulotomy incision with the first section A1 of the capsulotomy incision in the x/y plane 922 does not occur in such a measure as with fast z-scanning systems due to the high movement speed of the focus in the x/y plane 922.

The simple incision geometry or radiation geometry described up to now does particularly not ensure with slow lateral scanning movement in the x- and/or y-direction with respect to the eye movement that the capsulotomy takes place in an approximately circular manner. With a significant eye movement it can now occur that the third section A3 meets the first section A1 of the capsulotomy incision immediately at the beginning thereof and thus a significant dent and thus deviation from an approximately round capsulotomy 926 results, as shown in FIG. 16. A circular capsulotomy is however advantageous for improved centering of the intraocular lens (IOL) inserted later in the capsular bag 910-2 for many IOL types.

Therefore, the incision geometries suggested in FIGS. 17a to 17b are disclosed as alternatives, where, instead of a continuous incision, at least two temporally separately carried out incisions in the form of non-closed curves 927 take place, wherein each of the end regions 928-1, 928-2 of the non-closed curves is arranged within the capsulotomy 926 resulting later, thus within the circular opening.

Thus, as shown in FIGS. 17a and 17b, in a method for an incision guidance of a capsulotomy 926 by application of a short pulse laser system 200 for eye surgery, an opening can be generated in that focal points of a short pulse laser radiation by use of an x/y scanning system 240 are positioned in their x- and y-focal positions and thereby results a first non-closed curve 927-1 with a radius R in two steps and a second non-closed curve 927-2 with a radius R, and respectively with a first and a second end region 928-1, 928-2 of a respectively rectified curvature, wherein the first end portion 928-1 of the first non-closed curve 927-1 has a first end region radius $R_{E11}$ and the second end region 928-2 of the first non-closed curve 927-1 a second end region radius $R_{E12}$ and the first end region radius $R_{E11}$ as well as the second end region radius $R_{E12}$ is smaller than the radius R and the first end region 928-1 of the second non-closed curve 927-2 has a first end region radius $R_{E21}$ and the second end region 928-2 of the second non-closed curve 927-1 a second end region radius $R_{E22}$ and the first end region radius $R_{E21}$ and the second end region radius $R_{E22}$ is smaller than the radius R, all the end regions 927-1, 927-2 each have an end 929, and the first end portion 928-1 of the second non-closed curve 927-2 intersects the second end portion 928-2 of the first non-closed curve 927-1 and the second end region 928-2 of the second non-closed curve 927-2 intersect the first end region 928-1 of the first non-closed curve 927-1 in such a manner that the ends 929 of all end regions 928-1, 928-2 are arranged inside of a closed curve of the capsulotomy 926 formed by the first and the second non-closed curve 927-1, 927-2.

Also, in an advantageous manner, as shown in FIG. 17c, in a method for incision guidance of a capsulotomy using a short pulse laser system 200 for eye surgery, an opening of the capsular bag 910-2 can be generated in that the focal points of a short pulse laser radiation by use of an x/y scanning system 240 are positioned in their x- and y-focal positions, and thereby results in four steps a first, a second, a third and a fourth non-closed curve 927-1, 927-2, 927-3, 927-4 with a radius R, and each with a first and a second end 928-1, 928-2 of a respective rectified curvature, wherein the first end region 928-1 of the first non-closed curve 927-1 has a first end region radius $R_{E11}$ and the second end region 928-2 of the first non-closed curve 927-1 a second end region radius $R_{E12}$, the first end region 928-1 of the second non-closed curve 927-2 a first end region radius $R_{E21}$ and the second end region 928-2 of the second non-closed curve 927-2 a second end region radius $R_{E22}$, the first end region 928-1 of the third non-closed curve 927-3 a first end region radius $R_{E31}$ and the second end region 928-2 of the third non-closed curve 927-3 a second end region radius $R_{E32}$ and the first end region 928-1 of the fourth non-closed curve 927-4 a first end region radius $R_{E41}$ and the second end region 928-2 of the fourth non-closed curve 927-4 a second end region radius $R_{E42}$ has and all end region radii $R_{E11}$, $R_{E12}$, $R_{E21}$, $R_{E22}$, $R_{E31}$, $R_{E32}$, $R_{E41}$ and $R_{E42}$ are smaller than the radius R, wherein all end regions 928-1, 928-2 respectively have an end 929, and the first end region 928-1 of the second non-closed curve 927-2 intersects the second end region 928-2 of the first non-closed curve 927-1, the first end region 928-1 of the third non-closed curve 927-3 the second end region 928-2 of the second non-closed curve 27-2, the first end region 928-1 of the fourth non-closed curve 927-4 the second end region 928-2 of the third non-closed curve 927-3 and the second end region 928-2 of the fourth non-closed curve 927-4 the first end region 928-1 of the first non-closed curve 927-1 in such a manner that the ends of all the end regions 928-1, 928-2 are arranged in the inside of a closed curve of the capsulotomy 926 formed by the first, second, third and fourth non-closed curve 927-1, 927-2, 927-3, 927-4.

If the total incision of the capsulotomy 926, as described herein, and also executable with a higher number of non-closed curves 927-1 . . . 927-n, is distributed on several separately executed incisions, this leads to a shorter incision length for each of the non-closed curves 927-1 . . . 927-n. For a given lateral scanning speed in the x and/or y-direction, this leads to a shorter incision duration for a single non-closed curve 927-1 . . . 927-n. During this shorter incision duration the eye movements lead to a lower deviation from a circular incision curve for each of the separately executed incisions of a non-closed curve 927-1 . . . 927-n. Prior to the execution of a next incision, this can be laterally realigned. Even without such a realignment, this incision geometry is particularly, but not only advantageous for such short pulse laser systems 200, whose scanning system or scanning systems moves the focus of a short pulse laser radiation for cutting the capsular bag faster along the optical axis 215 than in the lateral direction, or which a lateral partial field scanner, as mechanical tolerances of the lateral scanner or the scanner guidance of the short pulse laser system 200 can be compensated better.

For each pair of intersecting non-closed curves 927-n−1, 928-n therefore applies: The intersection is located in a second end region 928-2 of a non-closed curve 927 (n−1) and a first end portion 928-1 following a non-closed curve 927-n and the radii of curvature of the end regions $R_{En1}$, $R_{En2}$ are smaller than the radius R of the non-closed curves 927-n−1, 928-n, which describes the radius of curvature of the central region of a non-closed curve 927-1, . . . 928-n between the two end regions 928-1, 928-2.

The requirement that the radii of curvature of the end regions $R_{En1}$, $R_{En2}$ should be less than the radius R thereby also includes the case that the radii of curvature of the end portions $R_{En1}$, $R_{En2}$ approach the radius of curvature R from below, thus $R_{En1}$, $R_{En2}$→R. All non-closed curves 927-n−1, 928-n have the radius R in their central region. Smaller, thus insignificant differences between the radii R of two non-closed curves 927-n−1, 928-n are however possible, without missing the target to generate a closed curve 926 by which the cooperation of the non-closed curves in the above described manner, which is designed approximately with a radius R, and thus fulfills the requirements for a capsulotomy incision. Further, the extension of the end regions 928-1, 928-2 between two non-closed curves 927-n−1, 928-n can also vary.

For a partial field scanner, it is thereby particularly advantageous if the number of the separate incisions, thus the number of the non-closed curves 927-1, . . . 928-n corresponds with the number of necessary partial fields corresponds for covering the total area of a capsulotomy 926.

Patient Interface/Contact Element

Figure 18:
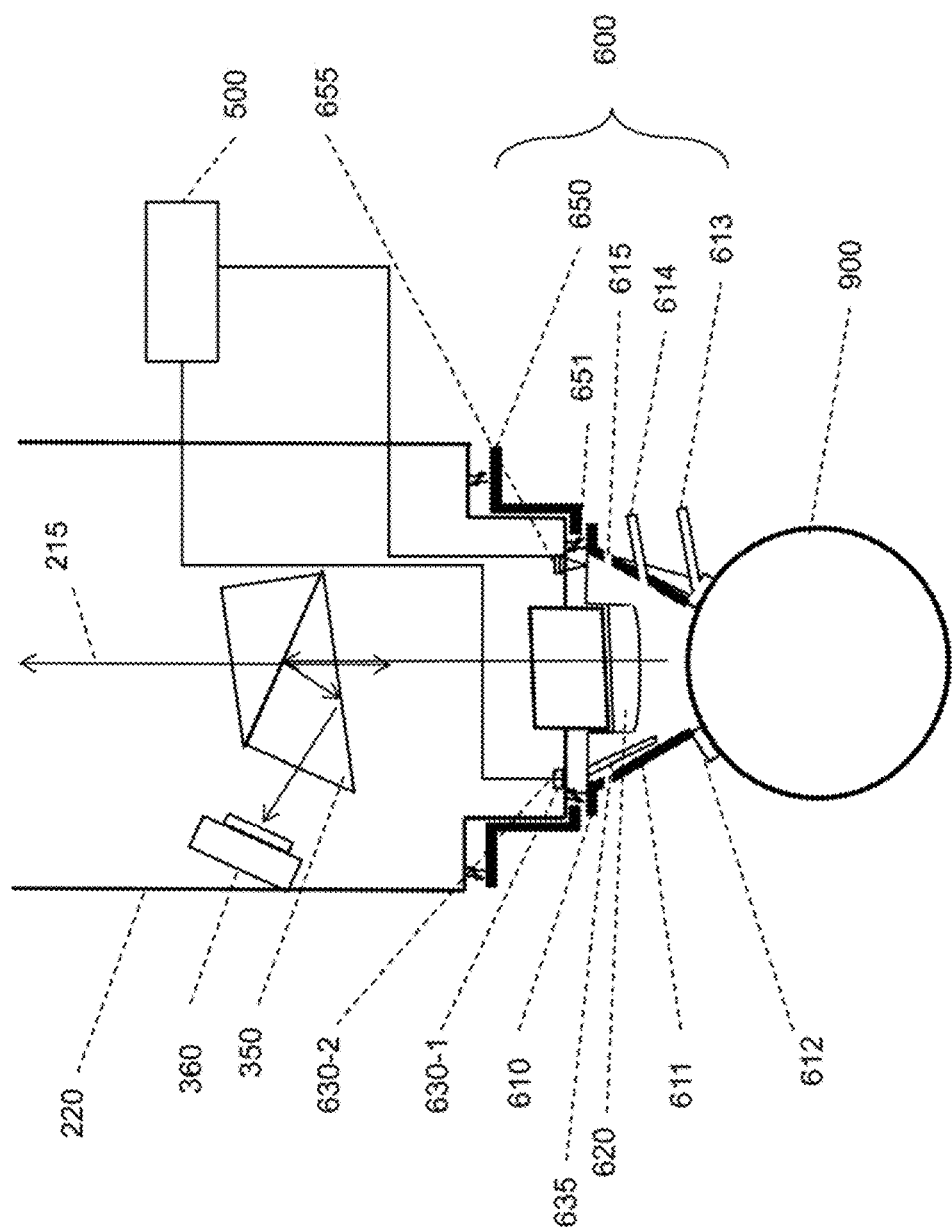
FIG. 18: a patient interface at a short pulse laser system for eye surgery.

In order to design the workflow for the operator as simple as possible, the patient interface 600 necessary for optical reasons containing a contact element 610—structure in FIG. 18 for processing the eye 900 by application of a system for short pulse laser eye surgery 100 is shown. The structure shown here includes a patient interface 600, an applicator head 220 of the system for short pulse laser eye surgery 100, wherein the patient interface 600 in FIG. 18 is fixed on the eye 900 of the patient as well as on the applicator head 220 of the system for short pulse laser eye surgery 100 and thus fixes the relative position of the eye 900 to the system for short pulse laser eye surgery 100 and, consequently, to the beam path of the short pulse laser radiation.

The patient interface 600 includes a contact element 610, which is designed as a liquid interface in this example embodiment. The contact element 610 is in one piece, manufactured, for example, from a uniform transparent material and contains a suction ring 612, a casing 611 and an optical element 620 at the top of the casing 611. It further comprises two openings 613, 614, to which the two leads are connected via fixing aids or permit the connection of two leads, wherein respectively one lead is or will be connected to one of the openings 613, 614.

A one-piece contact element 610, in which all the functional elements are integrated, allows a simpler handling than multi-component contact elements 610, which are only assembled on the patient's eye 900. Such multi-component contact elements 610 are described in e.g. the documents U.S. Pat. No. 7,955,324 B2, U.S. Pat. No. 8,500,723 B2, US 2013/053837 A1, WO 2012/041347 A1.

The two leads serve on the one hand for the application of a vacuum, here via the bottom opening 613, and on the other hand for feeding or removing fluid in the contact element 610, when the contact element 610 is docked to the eye 900, through the upper opening 614.

In an example embodiment, an overflow outlet 615 is further provided in the upper casing area of the contact element 610, distal to the eye 900, via which excess fluid or air can exit from the contact element 610 during filling.

In an example embodiment, the patient interface 600 contains a mechanically releasable coupling element 651 for the mechanical fixation of the contact element 610 on the applicator head 220. Alternatively, it is possible that the patient interface 600 contains a contact element 610 with a further suction structure instead of a mechanical interface with a mechanically releasable coupling element 651, manufactured of the same material as the contact element 610. This further suction structure holds the contact element 610 on the applicator head 220 when a vacuum is applied. As this is an alternative solution, it is not shown in FIG. 18.

It is also advantageous if a surface of the optical element 620 facing away from the casing 611 and facing the applicator head 200, is arranged not vertical but inclined to the optical axis 215.

Thereby it is avoided that, during the measurement of the eye structures by use of optical coherence tomography (OCT) through the contact element 610, the reflexes of an OCT short-coherence light source on the surface of the optical element 620, are directly reflected back into the OCT detection beam path and in a critical OCT-image area, and shine over the eye structure actually to be measured and thereby falsify them. This concern exists with a vertical orientation of the surface of the optical element 620 to the optical axis 215.

The surface of the optical element 620 facing the casing 611 and thus the eye 900 is preferably convexly curved. Thereby, an optical effect is achieved on the one hand, on the other hand, air bubbles which form travel along the curved walls upwards and to the edge or over the edge of the lens and thus outside the aperture of a short pulse laser radiation or of the OCT illumination and detection beam.

Furthermore, the surface of the optical element 620 facing the casing 611 and the eye 900 can be coated in a hydrophilic manner or be surface treated. Thereby, the wetting with water or another liquid, such as a "balanced salt solution" (BSS) and the migration of bubbles to the side is improved.

It is favorable, for example, if the surface of the optical element 620 facing the applicator head 220 is anti-reflection coated, so that the high intensity of the incident radiation short pulse laser radiation is not reflected back into the device optical system of the system for short pulse laser eye surgery 100.

A patient interface 600, which additionally contains an applicator head protector 650, which for example has a recess in the center, is advantageous for sterility. This applicator head protector 650 can be placed and fixed over the side of the applicator head 220 facing the eye 900, as shown in FIG. 18. This applicator head protector inhibits contamination of the applicator head 220 by e.g. fluids during surgery. The recess allows fastening of the patient interface 600 with the contact element 610 directly to the applicator head 220, so that the applicator head protector 650 does not present an obstacle in the beam path of the short pulse laser radiation between the system for short pulse laser eye surgery 100 and the optical element 620 of the contact element 610.

If the recess is thereby realized centrally in the applicator head protector 650, a spatially uniform protection of the applicator head 220 is achieved.

In an example embodiment, the contact element 610 and the applicator head protector 650 of the patient interface 600 are made as two separate or separable parts. An applicator head protector 650 separated from the contact element 610 has the advantage that different demands on the contact element 610, such as a high precision or geometrical and optical properties from those of the environment protection, such as a simple and cost-effective embodiment as possible can be realized separately, and thus be realized better.

In an example embodiment, the applicator head protector 650 is connected to the applicator head 220 by a mechanically releasable coupling element 651.

According to another example embodiment, the upper casing diameter of the contact element 610 is larger than the recess in the applicator head protector 650. Thereby, a complete protection for the applicator head surface is enabled.

In order to support the docking and in particular the lateral alignment of the application head 220, a particularly suitable illumination system for short pulse laser eye surgery is disclosed in FIG. 18: An optical wave guide structure 635 is admitted into the casing 611 of the contact element 610. In the applicator head 220 of a system for short pulse laser eye surgery 100, in turn, is integrated a light source 630-1, which emits visible light and/or a light source 630-2, which emits infrared light. In particular, during the surgical procedure using a short pulse laser radiation in the eye 900 in which the short pulse laser radiation is directed into the eye 900 via optical elements of the applicator head 220 and thereby the optical path in a microscope head 320 above is blocked 320 or affected, the eye 900 can for example be illuminated with the infrared light 630-2, and the infrared light reflected from the eye 900 can be guided via beam splitter prism 350, which selectively reflects infrared light, into a camera 360, with which infrared light can be detected. However, the prism 350 does not reflect the visible light or the wavelengths which are used by the short pulse laser source 210 or by the OCT light source 405. Light of these wavelengths not reflected by the prism 350 proceed without interference through the prism 350.

This construction has the advantage that, compared to the alternative solution, the illumination by an illumination present in the surgical microscope 300, no reflexes are added by the additional optical elements of the applicator head 220 situated in the illumination beam path and affect the image.

Furthermore, it is advantageous if a force sensor 655 is integrated in the applicator head 220, which is in contact with the contact element 610 during a docking of the patient interface 600. The force sensor 655 and the visible light-emitting light source 630-1 and the infrared light-emitting light source 630-2 are advantageously connected to a control device 500, which also controls the system for short pulse laser eye surgery 100, or with an additional control unit 500', which is in contact with the control device of the system for short pulse laser eye surgery 100 via communication paths.

The above arrangement then permits the following method of automatically switching of the illumination when docking the applicator head 220 to the eye 900:

(1) Switching the light source of the visible light 630-1 on
(2) Measuring the pressure and guiding the pressure signal through the force sensor 655 to the control unit 500
(3) Switching off the light source of the visible light 630-1 and switching on the light source of the infrared light 630-2 by the control device 500 as soon as the pressure signal of the force sensor 655 exceeds a predetermined value.

By this automated switching, it is prevented that the patient's eye 900 is illuminated permanently with visible light 630-1 possibly damaging the patient after the docking to the applicator head 900 by means of the patient interface 600 to the eye 900. An illumination of the patient's eye 900 then takes place with the less harmful infrared light 630-2.

Referencing and Registration

In order to be able to align transfer of preoperatively measured data e.g. the axial position of the preoperatively measured astigmatism of the eye 900 or the cornea 910 or the target position of access incisions or relaxation incisions compared to preoperatively measured astigmatism axes of the eye 900 or the cornea 910 correctly also during surgery on the eye, the preoperative data or desired target positions are fixed or referenced relative to preoperatively acquired reference marks or referenced in the state of the art. Thereby, artificially introduced markings such as dye-points or cornea incisions, but also naturally existing markings such as vascular structures in the sclera or iris structures or simply an overall image of the eye 900 with its existing structures are used as reference markings.

If a contact element 610 is used as in the laser cataract surgery, the problem results that these markings are often covered or influenced by the contact element 610, in particular by the suction ring structures 612 of the contact element 610.

To be able to also use the reference markings 640 or the referencing of the preoperative data or target positions connected with the markings with the use of a contact element 610, the following example embodiments are disclosed.

Figure 19B:
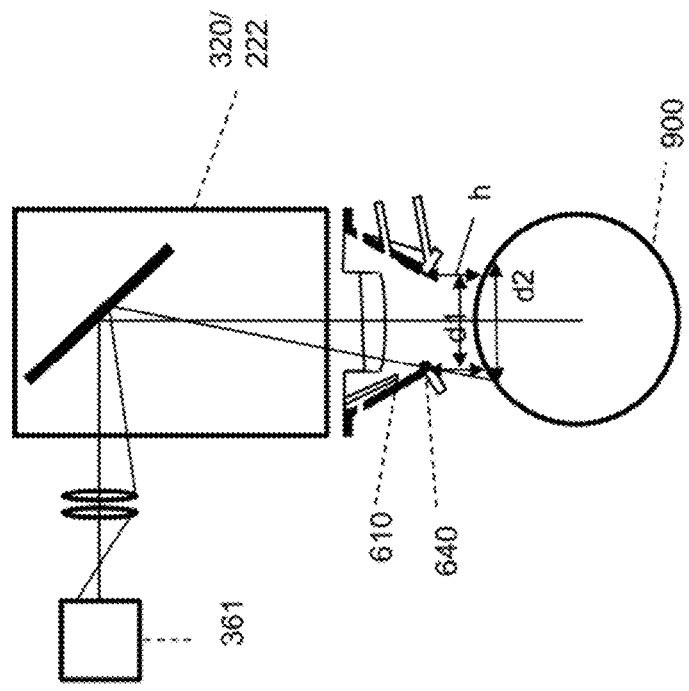
FIG. 19b: a second structure for referencing laser incisions with a patient interface at a short pulse laser system.
Figure 19A:
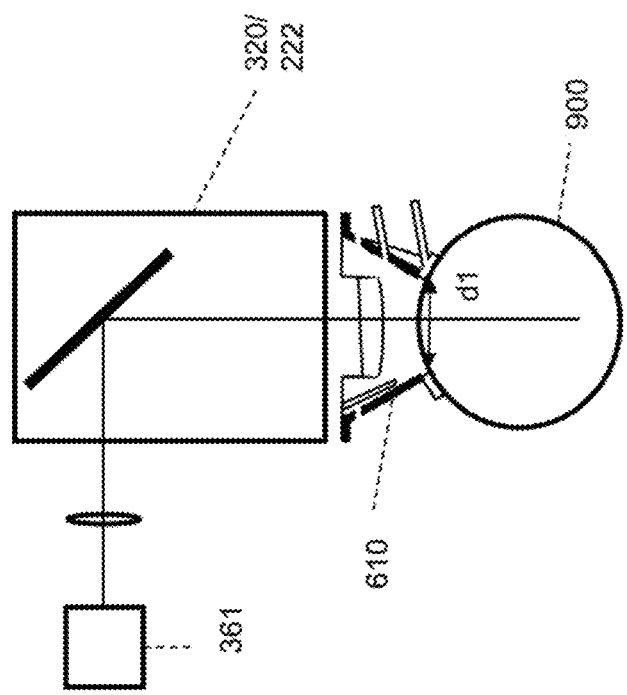
FIG. 19a: a first structure for referencing laser incisions with a patient interface at a short pulse laser system.

FIG. 19*a* discloses a first structure for referencing laser incisions with a patient interface 600 at a short pulse laser system 200. This structure contains a microscope head with an applicator head 320/220 or an applicator head 220, a camera 361 and a patient interface 600 with a contact element 610. The imaging beam path of the camera 361 is designed so that the field of observation detects the central part of the contact element 610, wherein the detected, free diameter d1 of the contact element 610 not covered by edges of the contact element 610 etc. is at least 14 mm.

Because of this large free diameter it is enabled that the undisturbed observation field is so great that sufficient pronounced and clearly visible markings or structures of the eye 900 are visible with the camera 361, and the referencing of the preoperative data or target positions can take place with sufficient certainty. However, for smaller eyes 900, such a contact element 610 can already too large for reliable practical application.

FIG. 19*b* thus offers a second structure for referencing laser incisions with a patient interface 600 on a short pulse laser system 200 in the undocked state. This structure contains a microscope head with an applicator head 320/220 or an applicator head 220, a camera 361 and a patient interface 600 with a contact element 610, which has at least one marking 640. The imaging beam path of the camera 361 is designed so that the observation field detects the central part of the contact element 610 and the marking 640, wherein the free visible diameter of the contact element d1 is at least 10 mm, preferably at least 11 mm, and the depth h in the image is at least at least 5 mm with a suitable magnification.

Because of the free diameter of the contact element 610 in conjunction with the depth of the image it is ensured that even in the undocked state of the patient interface 600 containing a contact element 610, the sharp field of view with a diameter d2 on the eye 900 is large enough in order to detect the preoperatively measured reference markings of the eye 900 in the field of view of the camera 361 in a sharp manner, and that the marking 640 of the contact element 610 is also visible in a sharp manner in the field of view.

With this or a similar construction, the method of the referencing for relaxation or access incisions in the cornea disclosed in the following is enabled, also see FIG. 20:

(1) Recording a first image of the eye 900 under illumination in the undocked state of the patient interface 600, with a contact element 610 at the patient's eye 900,
(2) Registering the position of the marking 640 of the contact element 610 relative to the reference markings of the eye 900 in the first image,
(3) Recording a second image of the eye 900 in the docked state of the patient interface 600 with the contact element 610,
(4) Aligning the short pulse laser incisions, for example by a femtosecond laser radiation, by use of the discernible position of the marking 640 of the contact element 610 in the second image and the registration obtained in step (2).

If the desired incisions relative to the reference markings can be fixed or referenced in the eye 900 by application of a preoperative diagnostics, the assignment of the incisions to the reference markings can take place with the aid of the above steps, even if they are no longer visible, but are covered by the contact element 610.

In one variant of the structure, the free diameter of the contact element 610 is larger than 13 mm, and even in the docked state of the contact element 610 to the eye 900, parts of the referencing markings necessary for the referencing in the eye 900 are still visible.

If this is the case, then the above method can be further improved by supplementing steps 1-3 of the above method by the following steps:

(4) Registration of the position of the marking 640 of the contact element 610 with respect to the visible reference structures of the eye 900 in the second image.

(5) Aligning the short pulse laser incisions, for example by a femtosecond laser radiation, by use of the position of the marking 640 of the contact element 610 or the visible reference markings in the second image present in the second image, provided that the registration of the position of the marking 640 compared to the visible reference markings of the eye 900 in the second image does not deviate from a predetermined amount of the registration of the position of the marking 640 with respect to the reference markings of the eye 900 in the first image.

A disadvantage of the above structure is that the optical system has to be designed elaborately on a large depth range.

FIG. 21a thus discloses a third structure for referencing laser incisions with a patient interface 600 at a short pulse laser system 200 in the undocked state. This structure contains a microscope head with an applicator head 320/220 or an applicator head 220, two cameras 361-1, 361-2 and a patient interface 600 with a contact element 610, which has at least one marking 640. The imaging beam path of the first camera 361-1 is designed so that it detects the mark 640 of the contact element 610 in a sharp manner, and the imaging beam path of the second camera 361-2 is designed so that it detects reference structures of the eye 900 in the undocked state in a sharp manner. In addition, the free visible diameter d1 of the contact element 610 is at least 10 mm, according to another example embodiment at least 11 mm.

Because of the free diameter of the contact element 610 in connection with the difference in the focal position in the image, it is enabled that, even in the undocked state, the sharp image field of the second camera 361-2 with a diameter d2 on the eye 900 is large enough to recognize the preoperatively measured reference markings of the eye 900.

The following method of referencing for relaxation or access incisions is revealed with this or a similar structure:

(1) Recording a first image of the contact element 610 with its marking 640 by the first camera 361-1 and virtually simultaneous or simultaneous recording of a second image of the eye 900 with reference markings of the eye 900 by the second camera 361-2 in the undocked state of the patient interface 600, which contains the contact element 610 with its marking 640, to the patient's eye 900.

(2) Registering the position of the marking 640 of the contact element 610 in the first image relative to the reference markings of the eye 900 in the second image with a known allocation of the alignment and magnification of the image fields of camera 361-1 and 361-2, predetermined by the structure.

(3) Recording a third image of the eye 900 in the docked state of the patient interface 600 with the contact element 610 containing a marking 640 by the first camera 361-1.

(4) Aligning the short pulse laser incisions, usually the femtosecond laser incision, by use of the recognizable position of the marking 640 of the contact element 610 in the third image and the registration obtained in step (2).

In a variant of this above structure and method, the first camera 361-1 is replaced by an imaging OCT system.

Alternatively, instead of using two cameras 361-1, 361-2 in parallel, only one camera 361 with sequential focus adjustment can be used.

FIG. 21b discloses such a fourth structure for referencing laser incisions with a patient interface 600 at a short pulse laser system 200 in the undocked state. This structure contains a microscope head with an applicator head 320/220 or an applicator head 220, a camera 361, a focusing lens 362 and a patient interface 600 with a contact element 610, which has at least one marking 640. The imaging beam path of the camera 361 is designed in such a manner that, at a first position of the focusing lens 362, the marking 640 of the contact element 610 is detected in a sharp manner by the camera, and at a second position of the focusing lens 362, the reference markings of the eye 900 are detected in a sharp manner in the undocked state. The free visible diameter d1 of the contact element 610 is thereby at least 10 mm, according to another example embodiment at least 11 mm.

Due to the free diameter of the contact element 610 in connection with the difference in the focal position of the image, it is enabled that even in undocked state the sharp field of view with the diameter d2 is large enough at the second position of the focusing lens 362 on the eye 900, in order to detect the reference markings of the eye 900.

The following method of referencing for relaxation or access incisions is disclosed with this or a similar structure:

(1) Recording a first image of the contact element 610 with its marking 640 with the camera 361 in a first position of the focusing lens and time-delayed, for example within seconds of recording the first image, recording a second image of the eye 900 with its reference marks by the camera 361 in a second position of the focusing lens, both in the undocked state of the contact element 610 containing the patient interface 600 to the patient's eye 900;

(2) Registering the position of the marking 640 of the contact element 610 in the first image relative to the reference markings of the eye 900 in the second image with a known allocation of the image fields of the camera 361 in the first and in the second position of the focusing lens 362 predetermined by the structure;

(3) Recording an image 3 of the eye in the docked state of the contact element 610 by the camera in or near the focal position 1;

(4) Aligning the fs incisions on the basis of the recognizable marking position of the contact element 610 in image 3 and the registering obtained in step (2).

Overall, all of the above structures and methods for referencing and registering are elaborate with regards to technical devices.

Figure 21C:
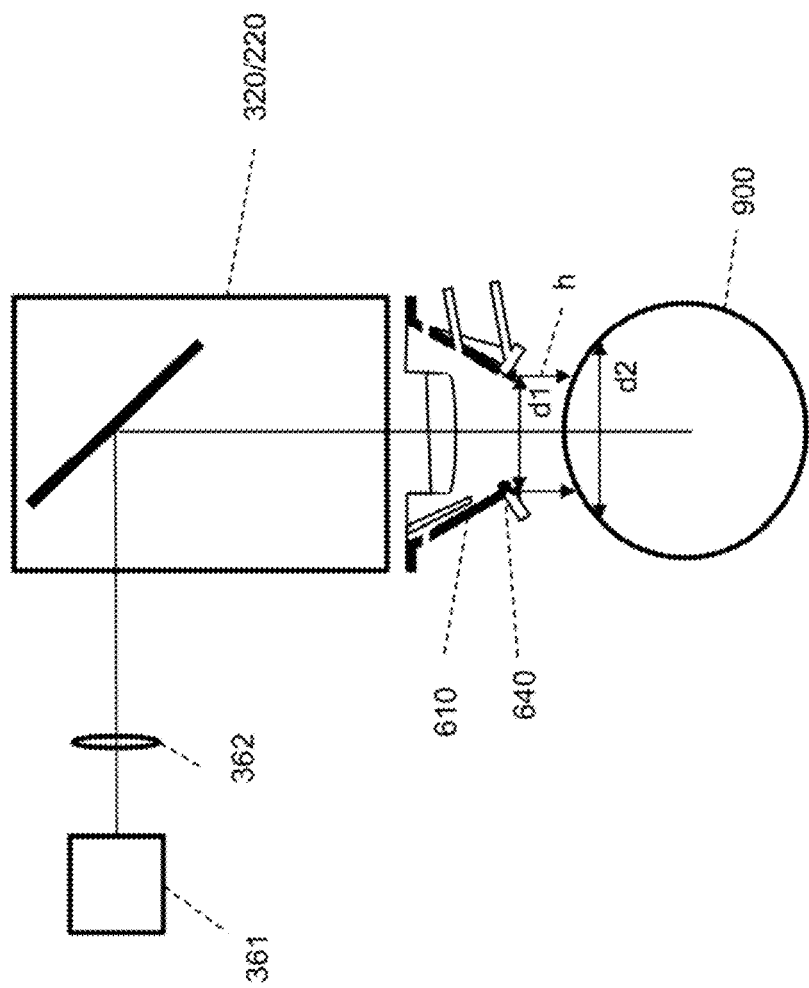
FIG. 21c: a fifth structure for referencing laser incisions with a patient interface at a short pulse laser system.

FIG. 21c thus discloses a fifth structure for referencing laser incisions with a patient interface 600 at a short pulse laser system 200 in the undocked state. This structure contains a microscope head with an applicator head 320/220 or an applicator head 220, a camera 361, a focusing lens 362 and a patient interface 600 with a contact element 610 that contains at least one marking 640. The imaging beam path of the camera 361 is designed so that the reference structures of the eye 900 are detected in a sharp manner in the undocked state, and that the free visible diameter d1 of the contact element 610 is at least 11 mm.

Because of the free diameter of the contact element 610 in connection with the focal position of the image it is enabled that, even in the undocked state with a distance h of the contact element 610 from the eye 900, the sharp field of view with a diameter d2 on the eye 900 is large enough to capture the reference markings of the eye 900.

With this or a similar structure, the following method of referencing for relaxation or access incisions is disclosed:
(1) Recording a first image of the eye 900 with reference markings by the camera 361 in the undocked state of the patient interface 600 with the contact element 610 at the patient eye 900;
(2) Docking and fixing a patient interface 600 with a contact element 610 to the eye 900 within a few seconds;
(3) Aligning the short pulse laser incisions on the basis of recognizable reference structures in the first image.

The above structures for referencing and registering also allow the orientation of intraocular lenses (IOL), after they have been inserted into the capsular bag 910-2, by use of reference markings, which are determined in a preoperative manner. Typically, this referencing of the orientation takes place at reference markings, which are recognized in pre-operatively obtained images of the eye 900 or at the preoperative images themselves. If these preoperative images of the eye 900 or their reference markers are registered with images or reference markings obtained in an intraoperative manner, thus the structures respectively contained therein are associated with each other and deviations are determined, the referencing of the orientation at the preoperative images and reference markings can be transferred by use of the registration on the image obtained in an inoperative manner or its reference markings.

When docking the patient interface 600 with the contact element 610, however, the appearance of the preoperative reference markings of the eye 900 or of the eye 900 itself are often changed. Thus, e.g. deformations and bleeding occur. Therefore, the registration of images of the eye 900 obtained preoperatively are susceptible to errors regarding the images of the eye 900 obtained in an intraoperative manner during the orientation of the intraocular lens (IOL).

This error susceptibility can be avoided as described below:

By means of the previous structures and methods for referencing and registration, the preoperative image is registered to an image of the eye 900, which is used for setting the short pulse laser incisions with a docked patient interface 600 containing the contact element 610. This image of the eye 900, which is used for setting the short pulse laser incisions with a docked patient interface 600 with the contact element 610, can then be viewed as a new reference image.

Now, after the short pulse laser surgery, that is after the patient interface 600 with the contact element 610 was docked to the eye 900, an image of the eye 900 is again recorded in the undocked state of the contact element 610. This image shows all the changed structures in the eye 900. The image can be registered with the same structures to the new reference image. It is registered in the further course of the surgery, namely when inserting the intraocular lens (IOL) and its orientation in the capsular bag 910-2 with an image of the eye 900, which was recorded during the orientation of the intraocular lens (IOL). Thereby, the referencing of the desired orientation of the intraocular lens (IOL) can be transferred to the preoperative images of the eye 900 through the chain of registrations of various images in a referencing of the desired orientation of the intraocular lens (IOL) to images of the eye 900 acquired intraoperatively during the insertion of the intraocular lens (IOL).

Figure 22:
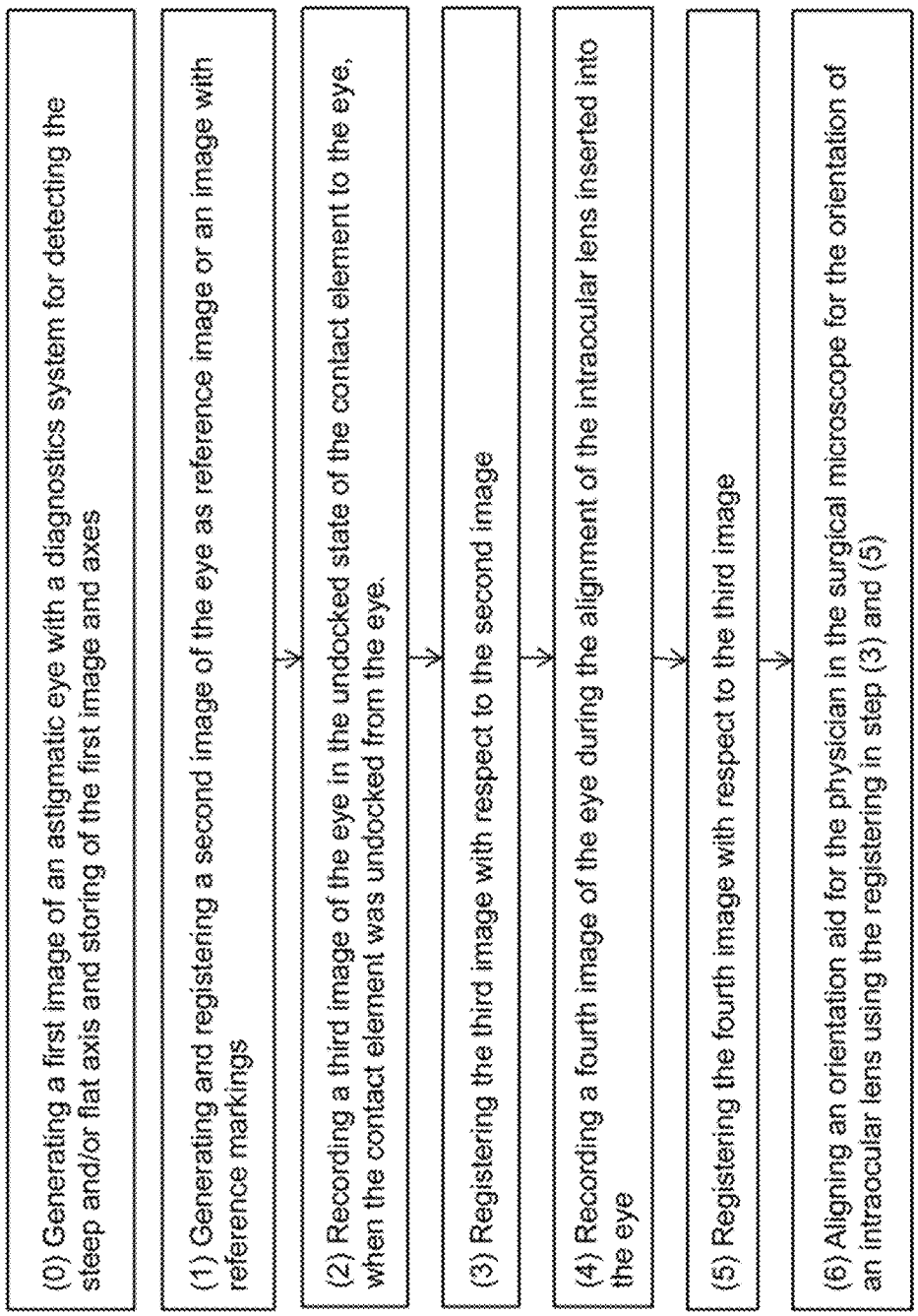
FIG. 22: a method for referencing the orientation of an intraocular lens when inserting into an eye.

For referencing the orientation of an intraocular lens (IOL) for a preceding short pulse laser cataract surgery, for example femtosecond laser cataract surgery of the lens, the following method is disclosed; see FIG. 22:

(0) Generating a first image of an astigmatic eye 900 with a (usually external) diagnostics system for detecting the steep and/or flat axis and storing of the first image and axes.
(1) Generating a second image, as reference image or an image with reference markings of the eye 900, for the orientation of a treatment at a patient interface 600 with a contact element 610 docked to the eye 900, e.g. according to the method described above;
(2) Recording a third image of the eye 900 in the undocked state of the contact element 610 to the eye 900, when the patient interface 600 with the contact element 610 was undocked from the eye 900;
(3) Registering the third image with respect to the second image;
(4) Recording a fourth image of the eye 900 during the alignment of the intraocular lens (IOL) inserted into the eye 900;
(5) Registering the fourth image with respect to the third image;
(6) Aligning an orientation aid for the physician in the surgical microscope 300 for the orientation of an intraocular lens (IOL) with the aid of registering in step (3) and (5).

The characteristics mentioned above and the characteristics explained in various example embodiments of the invention can thereby not only be in the exemplified combinations, but also in other combinations or alone, without leaving the scope of the present invention.

A description based on device characteristics applies with respect to these features analogously to the corresponding method, while method characteristics represent corresponding functional characteristics of the described device.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A patient interface for fixing a position of an eye relative to a system for short pulse laser eye surgery, the patient interface comprising:
a contact element;
wherein the contact element comprises a unitary one piece structure, formed of a transparent or partially transparent material and includes a suction ring, a casing and an optical element proximate an upper side of the casing; and
wherein the casing defines at least one opening, to which is connectable respectively a feed line via a fixing aid or which respectively permits connection of a lead; and
wherein the casing of the contact element further comprises an optical wave guide structure, wherein the optical wave guide structure is spatially displaced from a surface of the eye, and wherein the optical wave guide structure guides optical waves independently of the optical element.

2. The patient interface according to claim 1, wherein the casing defines two openings.

3. The patient interface according to claim 2, wherein the two openings include a first opening and a second opening, the first opening being in fluid communication with the suction ring whereby vacuum can be applied and the second opening being in fluid communication with an interior of the casing whereby fluid can be added to or removed from the interior of the casing.

4. The patient interface according to claim 1 wherein the casing further defines a further suction structure facing of the transparent material at the contact element on a side of the casing facing away from the suction ring.

5. The patient interface according to claim 1, wherein the optical element is arranged in an inclined manner relative to an optical axis of the system for short pulse laser eye surgery.

6. The patient interface according to claim 1, wherein a surface of the optical element facing the eye further comprises a hydrophilic coating or is surface-treated to make the surface hydrophilic and/or is convexly curved whereby migration of bubbles peripherally and upwardly and away from an optical aperture is facilitated.

7. The patient interface according to claim 1, wherein a surface of the optical element facing away from the eye comprises an anti-reflective coating.

8. The patient interface according to claim 1, further comprising an applicator head protector.

9. The patient interface according to claim 8, wherein the applicator head protector further defines a recess.

10. The patient interface according to claim 9, wherein the recess is located centrally in the applicator head protector.

11. The patient interface according to claim 9, wherein the recess is smaller than an upper casing diameter of the casing.

12. The patient interface according to claim 8, wherein the contact element and the applicator head protector are two separate or separable parts.

13. The patient interface according to claim 8, wherein the applicator head protector further comprises a mechanical coupling element that is adapted to releasably connect the applicator head protector with an applicator head of the system for short pulse laser eye surgery.

14. The patient interface according to claim 1, wherein the contact element comprises at least one marking.

15. The patient interface according to claim 14, wherein the at least one marking is located in a lower casing region of the casing.

16. The patient interface according to claim 1, wherein the contact element further defines an overflow outlet located in an upper casing area of the contact element via which excess fluid or air can exit the contact element during filling.

17. The patient interface according to claim 1, wherein the optical wave guide structure guides visible or infrared light to an interior of the casing by which the eye can be illuminated without adding reflections.

18. The patient interface according to claim 1, further comprising a further suction structure located proximate the upper side of the casing whereby suction can be applied to hold the contact element to an applicator head of the system for short pulse laser eye surgery.

19. The patient interface according to claim 1, wherein the casing defines a space structured to receive liquid, thereby causing the contact element to be designed as a liquid interface.

* * * * *

UNITED STATES PATENT AND TRADEMARK OFFICE
CERTIFICATE OF CORRECTION

PATENT NO. : 12,070,424 B2
APPLICATION NO. : 16/903758
DATED : August 27, 2024
INVENTOR(S) : Rill et al.

It is certified that error appears in the above-identified patent and that said Letters Patent is hereby corrected as shown below:

On the Title Page

Item [72], delete "Jena Ludwigsburg" and insert -- Jena --

In the Drawings

Fig. 11b, Sheet 10 of 20, delete "that the to" and insert -- that the --

In the Specification

Column 1, Line 7, delete "2017," and insert -- 2017, now U.S. Pat. No. 10,722,399, --

Column 2, Line 51, delete "suggested:" and insert -- suggested. --

Column 4, Line 40, delete "advantageously" and insert -- are advantageously --

Column 5, Line 6, delete "either are" and insert -- either --

Column 5, Lines 48-49, delete "photodisruption-," and insert -- photodisruption, --

Column 7, Line 61, delete "weight:" and insert -- weight. --

Column 8, Line 2, delete "avoid" and insert -- to avoid --

Column 9, Line 25, delete "to use" and insert -- use --

Column 11, Line 14, delete "act together" and insert -- act --

Column 11, Line 36, delete "plane in" and insert -- plane --

Signed and Sealed this
Eighteenth Day of March, 2025

Coke Morgan Stewart
*Acting Director of the United States Patent and Trademark Office*

CERTIFICATE OF CORRECTION (continued)
U.S. Pat. No. 12,070,424 B2

Column 13, Line 61, delete "of form" and insert -- from --

Column 14, Line 44, delete "of the" and insert -- the --

Column 16, Line 51, delete "a an" and insert -- an --

Column 16, Line 61, delete "and conducted" and insert -- and --

Column 21, Line 45, delete "order" and insert -- order to --

Column 25, Line 36, delete "surgicalmicroscope" and insert -- surgical microscope --

Column 27, Line 4, delete "unevennesses" and insert -- unevenness --

Column 27, Line 14, delete "housing 110:" and insert -- housing 110. --

Column 27 & 28, Lines 64-67 & 1-12, delete "FIG. 7 depicts an fs laser ............... and are focused in the eye 900" and insert the same at Line 65, as a new paragraph Column 28, Line 48, delete "that e.g." and insert -- e.g. --

Column 29, Line 28, delete "the then" and insert -- the --

Column 29, Line 30, delete "that that" and insert -- the --

Column 32, Line 43, delete "(by by" and insert -- (by --

Column 36, Line 4, delete "(see S1 ', S2', S3')" and insert -- (see S1', S2', S3') --

Column 36, Line 21, delete "incisionsurfaces" and insert -- incision surfaces --

Column 38, Line 25, delete "are the" and insert -- area of the --

Column 43, Line 20, delete "switching of" and insert -- switching off --

Column 44, Line 12, delete "too" and insert -- be too --

Column 44, Line 26, delete "at least at least" and insert -- at least --

Column 48, Line 4, delete "axes." and insert -- axes; --